(12) United States Patent
Guraschi et al.

(10) Patent No.: US 12,303,326 B2
(45) Date of Patent: May 20, 2025

(54) METHOD OF DETERMINING SCAN PLANES IN THE ACQUISITION OF ULTRASOUND IMAGES AND ULTRASOUND SYSTEM FOR THE IMPLEMENTATION OF THE METHOD

(71) Applicant: Esaote S.p.A., Genoa (IT)

(72) Inventors: Nicola Guraschi, Genoa (IT); Marco Crocco, Ovada (IT); Luca Zini, Genoa (IT)

(73) Assignee: Esaote S.p.A., Genoa (IT)

( * ) Notice: Subject to any disclaimer, the term of this patent is extended or adjusted under 35 U.S.C. 154(b) by 42 days.

(21) Appl. No.: 17/679,890

(22) Filed: Feb. 24, 2022

(65) Prior Publication Data
US 2022/0265242 A1    Aug. 25, 2022

(30) Foreign Application Priority Data
Feb. 25, 2021 (IT) .......... 102021000004376

(51) Int. Cl.
*A61B 8/08* (2006.01)
*A61B 8/00* (2006.01)
*A61B 8/14* (2006.01)

(52) U.S. Cl.
CPC ............ *A61B 8/0866* (2013.01); *A61B 8/085* (2013.01); *A61B 8/4245* (2013.01); *A61B 8/469* (2013.01);
(Continued)

(58) Field of Classification Search
CPC ..... A61B 8/0866; A61B 8/085; A61B 8/4245; A61B 8/469; A61B 8/483; A61B 8/5223; A61B 8/54; A61B 8/145; G16H 30/20; G16H 30/40; G06T 7/97; G06T 2207/30004; G06T 2207/30244; G06T 7/74; G06T 7/62; G06T 2200/04;
(Continued)

(56) References Cited

U.S. PATENT DOCUMENTS 9,380,999 B2 *  7/2016  Yoshida ................. A61B 8/481
10,123,778 B2 * 11/2018  Park ...................... A61B 8/0858
(Continued)

OTHER PUBLICATIONS

Mikla et al., "Medical Imaging Technology", 2014 (Year: 2014).*
(Continued)

*Primary Examiner* — Adil Partap S Virk
(74) *Attorney, Agent, or Firm* — Dickinson Wright PLLC

(57) ABSTRACT

Scan planes in acquisition of ultrasound images and dimensional measurements of objects represented in the images are determined by:
- defining a body to be examined and a predetermined orientation of the scan plane which intersects said body along which plane at least one ultrasound image is acquired;
- providing machine learning algorithm for verifying orientation and position of the scan plane, said algorithm trained with database of known cases which correlate image data of an image of a body previously examined and similar to said body with the position and orientation of the scan plane;
- reporting the scan plane does not correspond to the position and/or orientation of said predetermined scan plane;
- repeating the scan by changing the position and/or the orientation of the scan plane and repeating the steps as long as the position and orientation of the scan plane do not correspond to those of the predetermined scan plane.

11 Claims, 16 Drawing Sheets

(52) U.S. Cl.
CPC ............ *A61B 8/483* (2013.01); *A61B 8/5223* (2013.01); *A61B 8/54* (2013.01); *A61B 8/145* (2013.01)

(58) Field of Classification Search
CPC ....... G06T 2200/24; G06T 2207/10132; G06T 2207/10136; G06T 2207/20081; G06T 2207/20084; G06T 2207/30044
See application file for complete search history.

(56) References Cited

U.S. PATENT DOCUMENTS

| | | | | |
|---|---|---|---|---|
| 10,426,442 | B1* | 10/2019 | Schnorr | A61B 8/5223 |
| 10,646,156 | B1* | 5/2020 | Schnorr | G16H 30/40 |
| 10,964,424 | B2* | 3/2021 | Pagoulatos | A61B 8/565 |
| 11,534,143 | B2* | 12/2022 | Ebata | A61B 8/5223 |
| 2003/0009102 | A1* | 1/2003 | Quistgaard | A61B 8/00 600/446 |
| 2003/0212327 | A1* | 11/2003 | Wang | A61B 6/463 600/437 |
| 2004/0081340 | A1* | 4/2004 | Hashimoto | A61B 8/463 382/128 |
| 2005/0010106 | A1* | 1/2005 | Lang | A61B 6/4423 600/425 |
| 2005/0267366 | A1* | 12/2005 | Murashita | G01S 15/8993 600/437 |
| 2007/0238999 | A1* | 10/2007 | Specht | A61B 8/0891 600/437 |
| 2008/0110261 | A1* | 5/2008 | Randall | G01S 7/52023 73/64.41 |
| 2014/0058266 | A1* | 2/2014 | Call | A61B 8/4427 600/443 |
| 2015/0051489 | A1* | 2/2015 | Caluser | A61B 8/5207 600/440 |
| 2015/0133784 | A1* | 5/2015 | Kapoor | A61B 8/5246 600/438 |
| 2015/0253407 | A1* | 9/2015 | Nitta | A61B 6/5223 324/322 |
| 2015/0305718 | A1* | 10/2015 | Ogasawara | A61B 8/54 600/440 |
| 2017/0128045 | A1* | 5/2017 | Roundhill | A61B 8/5269 |
| 2018/0116633 | A1* | 5/2018 | Hansen | A61B 8/467 |
| 2018/0140282 | A1* | 5/2018 | Toyomura | G06V 10/82 |
| 2019/0000318 | A1* | 1/2019 | Caluser | A61B 5/0073 |
| 2019/0142390 | A1* | 5/2019 | Luo | G06T 7/73 600/437 |
| 2020/0049807 | A1* | 2/2020 | Pekar | G01S 7/5205 |
| 2020/0113542 | A1* | 4/2020 | Perrey | A61B 8/5207 |
| 2020/0134825 | A1* | 4/2020 | Li | G06N 3/045 |
| 2020/0345324 | A1* | 11/2020 | Matsumoto | A61B 8/54 |
| 2021/0038321 | A1* | 2/2021 | Toporek | G06V 10/764 |
| 2021/0204908 | A1* | 7/2021 | Perrey | A61B 8/463 |
| 2021/0251610 | A1* | 8/2021 | Stergiopoulos | G06V 10/26 |
| 2021/0290203 | A1* | 9/2021 | Xie | G01S 7/52053 |
| 2021/0327304 | A1* | 10/2021 | Buras | G06F 3/016 |
| 2021/0401407 | A1* | 12/2021 | Yang | A61B 8/5207 |
| 2022/0268612 | A1* | 8/2022 | Ito | A61B 8/06 |
| 2023/0329674 | A1* | 10/2023 | Ghani | G06T 7/0012 |

OTHER PUBLICATIONS

Search Report and Written Opinion dated Nov. 15, 2021, which issued in corresponding patent application No. IT202100004376.
Yuanwei Li et al.: "Standard Plane Detection in 3D Fetal Ultrasound Using an Iterative Transformation Network", arxiv.org, Cornell University Library, NY, Jun. 20, 2018, XP081414877, pp. 1-8.
Block Berthold: "Examination Technique and Equipment, Basic Physical and Technical Principles, Blood Vessels", In: "Abdominal Ultrasound: Step by Step", 2012, Thieme, Stuttgart, New York, XP055860065, pp. 2-18 and 35-37.

* cited by examiner

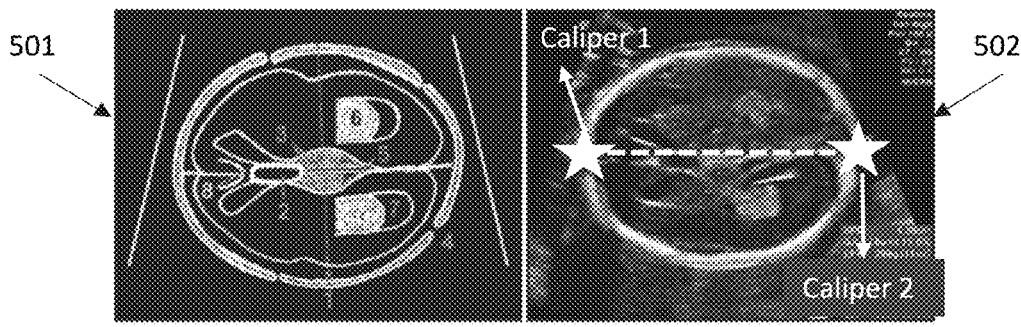

Biparietal diameter plane.

1 Biparietal diameter

2 Cavum Septum pellucidum

3 Thalami

4 Hypoechoic skull sutures

5 Third Ventricle

6 Choroid

Fig. 5

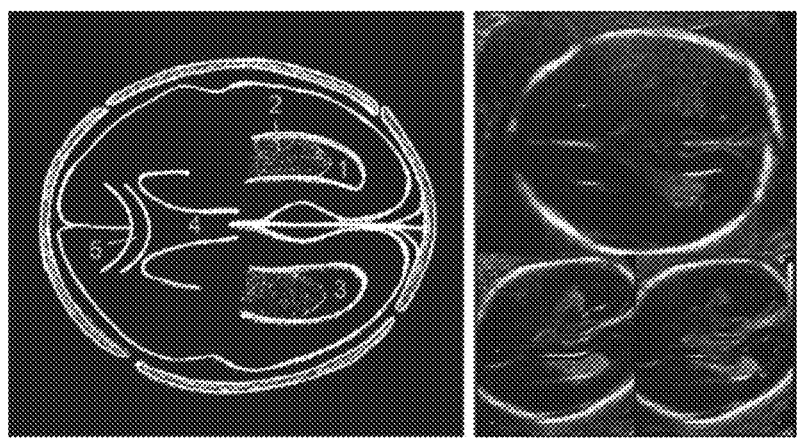

Transventricular plane.

The lower right images demonstrate that angling the fetal head can improve visualisation of the near field lateral ventricle.

1 Near field posterior horn of lateral ventricle

2 Choroid

3 Far field posterior horn of lateral ventricle

4 Cavum Septum Pellucidum (CSP)

5 Corpus callosum (CC)

Fig. 6

Cerebellar plane.

1 Cavum Septum Pellucidum

2 Cerebellar lobes

3 Cerebellar vermis

4 Cisterna Magna

5 Nuchal Fold

6 Cerebral peduncles

7 Falx

8 Thalami

Scan Plane Class

Fetal Head
- TransThalmic (BPD, HC, OFD)
- TransCerebellar (TCD, CM, CERV(Ita))
- TransVentricular (Ventr L)

Fetal Head

Fetal Body
- 1° Trim Very Early (1cm..)
- 1° Trim Crown Rump Lenght (CRL)
- 1° Trim NT or nasal Bone (coud be CRL zoomed)

Fetal Profile (2° Trim) (Manual label)
- Corpos Callosum
- Profile -> Good picture for the mum (good for starting 4D)

Fetal Body

Fetal Bones
- Bones FL, UL, RL, TL

Fetal Bones

Fetal Abdomen
- Abdomen AC
- Kidney (if labelled)

Fetal Abdomen

Fetal Heart
- 4CH
- 3VV
- ..

Fetal Heart

Fetal Spine (manual Label)

Other

Fig. 19

METHOD OF DETERMINING SCAN PLANES IN THE ACQUISITION OF ULTRASOUND IMAGES AND ULTRASOUND SYSTEM FOR THE IMPLEMENTATION OF THE METHOD

The present disclosure relates to a method of determining scan planes in the acquisition of ultrasound images and, in particular, for the determination of dimensional measurements of the objects represented in the images, and to an ultrasound system for the implementation of the said method.

The detection of the standard scan plane, for example, in the acquisition of fetal brain ultrasound images is a crucial step in the evaluation of fetal development. In combination with a 2D probe, this is currently performed by manually moving the 2D probe along the body under examination until the transmission beam emitted by the probe does not fall, i.e., is coincident with a scan plane that corresponds to the desired section image. An alternative mode involves the use of volumetric, i.e., 3D, imaging techniques and systems. In this case, the entire volume of the fetal brain is acquired, which contains among other things the image data along these standard scan planes. Therefore, the identification of the image along the desired scan plane takes place in real time or in a later phase, i.e., in the post processing phase, by choosing the image data from the set of data that constitute the volumetric image and that are related to the volumetric image contributions of the structures that fall on the desired scan plane. The manual identification of the standard plane in the 3D volume is laborious and requires an extensive knowledge of the fetal anatomy.

The determination of the correct scan plans not only in the case of fetal brain analysis, but also in other cases, both applied to the condition of the fetus and to diagnostic investigations of adult organs, is however always affected by an inaccuracy that the human eye cannot easily detect and that is due to positioning tolerances of the acquisition plane. In fact, the techniques for determining the correct position of the scan plane for carrying out dimensional measurements of the objects represented on the image corresponding to said plane are based on the fact of detecting specific anatomical structures that have to be simultaneously visible in a certain way in the scan plane image. These anatomical reference points or markers can however be present in the images of scan planes that fall within a certain range of tolerance related to the position and orientation with respect to the optimal plane, in particular with regard to the investigation, i.e. the measurements to perform on the scanned image.

The conventional way of acquiring scan planes therefore requires a thorough knowledge of anatomy, for example, of the fetal anatomy in the case of fetal imaging, and an intensive manual work. Therefore, automatic approaches are in great demand in clinical practice.

For this reason, methods and systems have recently been proposed that provide approaches based on machine learning algorithms for image analysis and the determination of the optimal scan plane from a set of volumetric image data corresponding to the volumetric image that contains the zone of interest and therefore the section along the scan plane of interest.

Thanks to these algorithms it is possible to encode the skills and experience of the specialist in identifying the correct scan plan in a database that constitutes the training database of the algorithm and to use this database to let the algorithm determine the desired scan plane, i. e. the contributions of the acquired image data which fall on said scan plane and which therefore relate to the anatomical structures reproduced along the section of said structures coinciding with said scan plane.

The treatment of diagnostic images by means of algorithms is known in the state of the art, for example in order to analyze and suggest indications of interpretation of the objects represented in an image. These techniques are summarized by the name CAD (Computer Aided Diagnostics). These algorithms are partly constituted by algorithms proposed for other purposes and related, for example, to activities such as the generic recognition of images, that is, of what is represented in them.

Examples of machine learning algorithms used in automatic image analysis are predictive algorithms, including neural networks, genetic algorithms, classification or clustering algorithms and others. The previous list is not to be considered exhaustive as a very large number of machine learning algorithms are currently available, used both separately and also in a combination of two or more algorithms.

The most important limit of these algorithms lies in the computational burden that can also involve in some cases relatively long calculation times that therefore has repercussions on the functionality of the ultrasound scanner for producing the final results and therefore on the duration of the examination from image acquisition to report issue. This partially reduces the advantage of the diagnostic technique by means of ultrasonic images which lies among other things in the ability to produce diagnostically useful images in real time and therefore reduces the costs and time of the examination itself.

The present invention is therefore based on a method and an ultrasound system of the type described at the beginning, i.e. a method and a system for determining scan planes in the acquisition of ultrasound images and in particular for determining dimensional measurements of the objects represented in the images, which method comprises the following steps:

a) defining a body to be examined and defining a predetermined orientation of the scan plane which intersects said body along which plane at least one ultrasound image is acquired;

b) providing a machine learning algorithm for verifying the orientation and the position of the scan plane along which the said ultrasound image has been acquired, said algorithm being trained with a database of known cases which uniquely correlate the image data of an image of a body examined in previous instants of time and which is similar to said body to be subjected to examination with the position and orientation of the scan plane along which said image was acquired relative to said body examined at said preceding instants, said position and said orientation of said scan plane corresponding to said predetermined position and/or said predetermined orientation;

c) scanning the said body to be examined by acquiring at least one ultrasound image along at least one scan plane that intersects the said body and has a position and orientation with respect to it;

d) analyzing the image data relating to the said at least one image along the said at least one scan plane by means of the said machine learning algorithm and establish whether the position and/or the orientation of the said scan plane along which the image has been acquired corresponds to the position and orientation predetermined for the said scan plane with respect to the body to be subjected to examination and/or if the scan plane along which the image was acquired coincides with the scan plane having said predetermined position and/or said predetermined orientation;

e) storing the image data of the acquired image and/or submitting said image to further processing if the scan plane along which said image has been acquired corresponds, within certain tolerances, to the scan plane having the said predetermined position and/or the said predetermined orientation;

f) reporting that the scan plane along which said image was acquired does not correspond, within certain tolerances, to the position and/or orientation of said predetermined scan plane;

g) and/or repeating the scan by changing the position and/or the orientation of the scan plane along which the image is to be acquired with respect to the position and/or orientation of the scan plane used in the acquisition of the previous image and repeating the steps from c) to g) as long as the position and orientation of the scan plane along which an image is acquired which is calculated in step d) do not correspond to and/or do not coincide with the position and/or orientation of the predetermined scan plane.

According to a first embodiment, the said method is performed in combination with an ultrasound probe that acquires two-dimensional images and in which the position of the probe and/or its inclination with respect to the body to be examined define the position and/or orientation of the scan plane; in this case it is possible that the verification of the position and/or orientation of the scan plane is performed in real time with the acquisition and that the result of this verification is shown to the user.

According to an embodiment, said information is purely informative, i.e. an indication relating to the fact that the position and/or the orientation of the scan plane do not correspond to the position and/or the orientation of the scan plane desired for the examination in progress and that the user must therefore change the position of the probe, the said verification being performed for each new position and/or each new orientation of the probe as long as the verification detects the correspondence or coincidence of the position and/or of the actual orientation with the desired position and/or orientation, this condition being signaled by an appropriate information message. In this case, according to an embodiment, to the user is asked to give a command for the possible subsequent steps which may consist in the storage of image data and/or even in the execution of processing or extraction processes of features from said image data. An alternative variant provides that in the aforementioned case of correspondence and/or coincidence of the actual position and/or orientation with the desired position and/or orientation, one or more subsequent steps such as storing the image data acquired along the said scan plane and/or the execution of processing and/or extraction steps of characteristics from said image data are activated and executed automatically and that such activation and/or execution is simply signaled to the user.

An embodiment may provide in combination with the features of the preceding embodiment and/or with one of the variants provided in combination with the embodiment that the information to the user may contain indications and/or suggestions on how to modify the position and/or orientation of the probe to bring the scan plane generated by the same to approach at least or to coincide with the desired position and/or with the desired orientation of the scan plane.

It is possible to provide any type of graphic interfaces and/or interfacing by means of a keyboard with the user, and the presentation method of the informations can be performed both in passive mode by the user or in a dynamic way, leaving the user the choice between different options for displaying or executing the method steps.

An alternative embodiment provides for the use of a three-dimensional ultrasound probe, i.e. a probe capable of acquiring a volumetric images of a body to be subjected to examination or of a limited region of the same.

According to an embodiment, in combination with the acquisition of a volumetric image, the image data are stored and processed at a later time, that is, in a subsequent post-processing phase and also separate from the acquisition phase.

According to a variant of this post-processing phase, the image data of the acquired volumetric image (3D) are subjected to processing by means of a machine learning algorithm, which algorithm is trained thanks to the aforementioned database of known cases to identify which data contributions of the volumetric images fall on a section plane of the acquired volume of the examined body, or which of the voxels that make up the three-dimensional set of image data of the volumetric image fall on said section plane, which section plane presents the desired predetermined position and/or the desired predetermined orientation.

Once the said set of voxels which fall on the section plane has been selected, it is possible to continue with the execution of the further method steps according to one or more of the preceding claims.

Therefore, according to this embodiment, the method of determining scan planes in the acquisition of ultrasound images and, in particular, for the determination of dimensional measurements of the objects represented in the images defined in its generic form above includes the following steps:

a) defining a body to be examined and defining a predetermined orientation of the scan plane which intersects said body along which plane at least one three-dimensional ultrasound image is acquired;

b) provide a machine learning algorithm for the identification of image data that fall on a scan plane that extends along a section plane having a desired position and/or the desired orientation with respect to said body under examination and which plane intersects said three-dimensional ultrasound image, said algorithm being trained with a database of known cases which univocally correlate the image data of an image of a body examined in previous instants of time and which is analogous to said body to be subjected to examination, with the position and the orientation of the scan plane along which scan plane the contributions of the image data or the voxels of the said acquired three-dimensional image fall;

c) performing the three-dimensional scan of said body to be subjected to examination;

d) identifying the contributions to the image data that fall along the said at least one scan plane by means of the said machine learning algorithm and generate a set of image data along the said scan plane;

e) storing the image data identified as falling along said scan plane and/or subjecting said image to further processing.

According to an embodiment said method further comprises the steps of:

f) calculating the reliability of the identification of said image data with reference to the scan plane and report this value to the user;

g) repeating the acquisition of the volumetric image and/or the recognition/identification step of the image data contributions (voxels) that fall on the said scan plane and perform step f) in relation to the newly identified image data contributions;

h) carrying out step g) until the fitness value falls within a predetermined range of values;

i) proceeding with step e) if the fitness value falls within said predetermined range of values.

In the previous description, the term image data refers both to the pixels or voxels of an image reconstructed from the signals received by the probe, and to said signals generally at radiofrequency (hereinafter referred to as RF signals) or raw data.

The above types of data differ in that the RF signal is an electrical signal which is generated by the transformation by the electro-acoustic transducers of the acoustic signals received by said transducers. These data are also subjected to so-called beamforming processes which have the purpose of identifying the contributions of the received signals due to reflectors having a position inside the body under examination along a scan plane or in a scan volume.

Other extraction and refinement processes of said signal contributions are possible and depend on the various methods of extraction of the image data present in the state of the art. Each of said known methods and/or a combination of the same can be used in combination with the method of the present invention. This also applies to the generation processes of the signal beams transmitted by a probe, i.e. the ultrasonic signal beams emitted by the probe and directed to the body under examination which can be realized according to any technique known from the state of the art and/or according to combinations of these known techniques.

As regards the methods of acquiring volumetric images, at the state of the art there are various methods and systems for acquiring three-dimensional ultrasound images, including for example:

methods in which, thanks to a system for detecting the position and/or orientation of a probe of the type suitable for acquiring two-dimensional images, a series of two-dimensional images is acquired along scan planes adjacent to each other, by moving the probe along a predetermined path and by tracing the position and orientation of the probe along said displacement path with respect to a reference system and wherein the image data are grouped along said adjacent scan planes in a three-dimensional image thanks to the knowledge of their relative position detected by the tracking system of the probe;

the provision of a probe formed by a two-dimensional array of transducers which therefore generates a beam having an opening along two mutually transvers directions, so that the acquired image is relative to the volume that falls within said opening of the probe;

the acquisition of three-dimensional images by steering of the beam generated by said probe along a two-dimensional sphere sector (segment).

These techniques or combinations thereof can be used in combination with one or more of the embodiments and variants described above.

In relation to the combination of the method according to the present invention which provides for the acquisition of a three-dimensional image of a body under examination or of a region of the same, it is possible to provide an alternative to a post-processing in order to determine the contributions of the image data that fall on a specific scan plane that intersects the body under examination and/or its representation in the volumetric image, also a processing step in real time.

According to a variant of implementation that can be applied to each of the aforementioned embodiments and variants of implementation and that for each of them allows to reduce processing times and to execute the method in real time without the need for waiting times between the single steps of said method that could make the examination and processing of the desired image data less fluid, it is foreseen to perform the processing steps on a selected subset of the acquired image data and/or alternatively or in combination with each other to perform certain steps such as the determination by means of the machine algorithm learning of the correspondence between the position and orientation of the actual scan plane with the position and orientation of the desired scan plane and/or the identification in the image data set of a 3D (volumetric) image of the related image data to the contributions that derive from or fall on a predetermined scan plane that intersects the said 3D image, using the raw data as image data, i.e. the RF data or using as image data the data relating to the pixels or voxels of the image obtained from said raw data, i.e. from RF data according one of the variants defined above.

Several alternatives are possible which allow to reduce the computational load and therefore the execution speed of the method.

According to an embodiment, the verification of the position and/or of the orientation of the scan plane or the identification and selection of the image data of a three-dimensional image which falls on a predetermined scan plane which intersects said volumetric image are performed on the image made up of individual pixels or voxels.

According to a variant it si possible to reduce the number of pixels or voxels along the scan plane by known resolution reduction and/or image compression techniques.

Once the correct scan plane has been identified and/or the pixels or voxels of a volumetric image which fall on a predetermined section plane have been identified and selected, the steps of image data processing and/or of features extraction can be performed by returning to the higher resolution and/or decompressing the image along the desired scan plane at the original resolution or even using for the processing and/or the extraction of features the image data in the form of raw data, or of the corresponding RF signals.

According to an embodiment, prior to the steps of verifying the position and/or orientation of the scan plane or of the identification and/or selection of the pixels or voxels of a volumetric image which fall on a desired scan plane, the step is provided of selecting a subset of scan planes and/or a subset of image data that fall into a limited region and/or a limited region of the body under examination, i.e. a ROI, which contains the target regions and/or the target structures and/or the target tissues.

The position and/or the orientation of said ROI can be determined for example on the basis of the recognition of predetermined characteristic markers of anatomical structures present in the body under examination and close to or coinciding with the desired scan plane.

The recognition of the said structures or of the characteristic markers, can be performed on the basis of a processing of the image data in any of the forms defined above, possibly modified or compressed to a resolution lower than that of acquisition.

For this step it is possible to use state-of-the-art image processing algorithms, such as autocorrelation algorithms, both statistical and deterministic classification algorithms and also machine learning algorithms.

According to an embodiment, these ROIs can be defined by means of so-called bounding boxes, whose size, position and orientation are defined by the anatomical and morphological structure of the body under examination and by markers consisting of characteristic elements of this structure.

In relation, for example, to this executive variant it is possible to foresee a fast acquisition at low resolution is provided which is subjected to a processing for the determination of the size, position and orientation of a ROI in the form of a bounding box, a subsequent acquisition with higher resolution of the image of the region included within the bounding box.

The data related to this second scan can be used by reducing the resolution or compressing them for the verification of the correctness of the scan plane or for the determination and selection of the image data contributions that fall on a scan plane included within the bounding box, while subsequently the data at the original resolution and/or the data in the form of RF signals along the scan plane validated by the aforementioned verification and/or along the predetermined scan plane inside the volumetric image of the bounding box can be used for carrying out the steps of storing and/or processing and/or extracting characteristics.

According to an embodiment, the present invention is applied to the obstetric field and in particular to the acquisition of ultrasound images for carrying out measurements of characteristic quantities of organs of the phoetus and hence for the estimation of the phoetal weight or other characteristics of the same.

Typical anatomical areas for which these measurements are performed on the basis of ultrasound images are for example the head of the foetus, the body of the foetus, the bones of the foetus, the abdomen of the foetus, the heart of the foetus and the vertebral column.

In order to allow a reliable measurement, the images on which said measurements are performed are acquired along scan planes which intersect adjacent anatomical organs or structures and which constitute anatomical markers of positioning and orientation of the scan plane. When all the structures provided as markers are present in an ultrasound image taken along a scan plane, the position and orientation of said plane are the correct ones in order to obtain reliable measurements from said images.

FIG. 19 shows a table containing some examples of classes of acquired images and the measurements that can be made on these images.

In an embodiment of the invention, therefore, the further processing foreseen in step g provides for the determination of the anatomical and dimensional measurements of the organs or structures of interest present in said image from the image data acquired along the desired scan plane.

According to an embodiment, the execution step of the measurements is preceded by a filtering and/or segmentation step of the image and therefore of recognition of the structure to be measured and of the contours of said structure.

This step can be performed using different types of algorithms known at the state of the art and also using a machine learning algorithm that has been trained with a database whose records associate acquired images and corresponding segmented images relating to cases known and validated by qualified expert.

According to one embodiment, once the steps of determining the image along the desired scan plane have been performed and this condition is verified according to one of the embodiments of the method described above, the image is shown on the screen to the user and is blocked (freeze) giving the user the possibility to visually evaluate whether or not all the anatomical markers provided for the desired scan plane are present in the scan plane.

According to an embodiment it is possible to give the user the option to confirm the image shown or to reject the image and to re-launch the acquisition steps according to one or more of the embodiments described above.

If the image is confirmed, it is possible to allow the user to perform the measurement steps in manual mode, i.e. by indicating the measurement reference points, or to allow the system to perform an automatic measurement.

In both cases, it is advantageous that the manually or automatically selected reference points and lines along which measurements are taken are highlighted and superimposed on the image shown on the display.

In manual mode, the definition of reference points and/or measurement lines between these points can be selected using a mouse with clicking and pointing operations or using a touchscreen directly with the fingers of the hand.

Further features of the method according to one or more of the preceding embodiments and/or according to one or more of the variants of embodiments described above are the subject of dependent claims.

The object of the invention is an ultrasound system for the implementation of the said method of determining scan planes in the acquisition of ultrasound images and in particular for the determination of dimensional measurements of the objects represented in the images according to one or more of the embodiments and/or variants described above.

This ultrasound system comprises:
  an ultrasound probe for transmitting beams of ultrasonic pulses in a body under examination and for receiving the ultrasonic pulses reflected by said body under examination, said probe being composed of a set of electroacoustic transducers arranged according to a predetermined design;
  a unit for generating excitation signals of the electroacoustic transducers of said probe to cause the emission of the ultrasonic transmission pulse beams;
  a unit for receiving the reception signals produced by the electroacoustic transducers as a result of the incidence on them of the ultrasonic reflection signals;
  a unit for forming the transmission beams that synchronize the excitation signals supplied to the individual translators in relation to each other, to focus the beam generated by the set of electroacoustic transducers on individual points and/or lines and/or areas of the body under examination;
  a unit for forming the reception beams which synchronize the reception signals to combine to each other the signal contributions of the individual transducers generated by reflection signals deriving from identical points and/or regions of reflection of the body under examination;
  a unit for extracting image data reception signals in form of radio frequency signals;
  a unit for generating a digital image from said image data in the form of radio frequency signals;
  a unit for displaying said digital image;
  a user interface that allows the user to enter commands and/or data and the system to display information data for the user;
  a unit of measurement of dimensional quantities of structures present in an image, which unit of measurement includes:
  devices for defining points and/or lines and/or reference surfaces for the execution of one or more different dimensional measurements relating to said points to said lines and/or to said reference surfaces;

an algorithm for determining the quantities and/or positions of said points, of said lines and/or of said reference surfaces.

According to the invention, ultrasound system further comprises a unit for processing and verifying the position and/or orientation of the scan plane of one or more scanned images, which unit is configured to perform a verification of correspondence of the position and/or orientation of the scan plane of the said images acquired with the position and/or orientation of a predefined scan plane, said verification being carried out by means of an image data analysis algorithm of the acquired image with image data of a database of image data relating to a plurality of separate acquisitions for which the correspondence of the position and/or orientation of the scan plane with the desired scan plane is known, said analysis algorithm being encoded in the form of instructions in a program which is executed by a processor of said processing unit.

According to a preferred embodiment, said processing unit for verifying the position and/or the orientation of the scan plane comprises a unit for generating information data on the outcome of the verification, which unit it is in communication with the user interface and/or with said display unit and displays said information data in a format that is intelligible by the user;

the said processing unit being provided with an input interface for a confirmation of acceptance and/or for a repetition and/or interruption command of the said verification activity.

According to yet another embodiment that can be provided in any combination or subcombination with the previous ones, said processing unit is provided with an input interface for a confirmation of acceptance and for a manual command to activate a process for extracting information and/or characteristics from the data image of images for which confirmation has been sent to the processing unit.

According to yet another feature that can be included in any combination or subcombination, a program for carrying out the process of extracting information and/or features from the image data is loaded into said processing unit, which program contains instructions for said processing unit for the execution of the steps of said information and/or characteristics extraction process and which program is loaded and launched for execution automatically by the same processing unit following the positive outcome of the position and/or position verification of the orientation of the scan plane or following manual confirmation by the user regarding the outcome of the aforementioned check.

The system according to one or more of the preceding claims is particularly suitable in combination with ultrasound probes that acquire two-dimensional images.

According to a variant, the system provides a probe or a probe/tracer group for the acquisition of a volumetric or three-dimensional image of the body under examination, and in combination with the same probe there is provided a processing unit in which a program is loaded and which executes the instructions which make said processor suitable for determining and selecting the contributions to the image data of the volumetric image which are derived from a predetermined scan plane having a desired position and/or a desired orientation with respect to said volumetric image and generate an image relative to said predetermined scan plane.

According to a possible further feature, said image along said predefined scan plane is displayed by means of said display unit.

Also in this variant, said processing unit is provided with an input interface for a confirmation of acceptance and/or for a command for repetition and/or interruption of said activity of determination and selection of said contributions to the image data of the volumetric image.

Still similar to the previous embodiment, said processing unit is provided with an input interface for a confirmation of acceptance and for a manual command to activate a process for extracting information and/or characteristics from the data image of images for which confirmation has been sent to the processing unit.

Even in this embodiment and in combination with any variation of the same, a program for carrying out the process of extracting information and/or features from the image data is loaded into said processing unit, which program contains instructions for said processing unit for the execution of the steps of said information and/or characteristics extraction process and which program is loaded and launched for execution automatically by the same processing unit following the positive outcome of the position and/or position verification of the orientation of the scan plane or following manual confirmation by the user regarding the outcome of the aforementioned check.

Similarly to what expressed for the first embodiment, the steps of determining and/or selecting the contributions to the image data of the volumetric image which are derived from the scan plane having the desired position and/or the desired orientation with respect to the volumetric image, or to the part of the body under examination represented therein can occur using different types of algorithms and/or combinations of algorithms, according to what has already been previously disclosed for the method.

In particular, it is possible to use machine learning algorithms that have been trained using databases of known cases to each of which is associated a record in which are stored the contributions to the image data of the volumetric image that are derived from the scan plane having the desired position and/or orientation with respect to the volumetric image, i.e. the part of the body under examination represented therein related to cases that have been checked for correctness.

In an embodiment, this database and the corresponding algorithm are updated by adding to the database the data concerning each further processing carried out by the algorithm and by training the algorithm on the basis of this new updated database.

In combination with any of the above-described embodiments and corresponding embodiments or improvements, the system according the present invention comprises a processing unit for the definition of one or more ROIs into which one or more of the regions and/or structures represented in the acquired images fall and which are common to the region and/or to the structures which identify a predetermined scan plane having a desired position and/or a desired orientation with respect to the body under examination.

Such a unit may consist of an independent processing unit into which is loaded a software and which executes a software comprising instructions to perform the aforementioned activity of defining the ROI(s), or this software is loaded and executable by a single processing unit such as that for verifying the scan plan and/or that for determining and/or selecting the contributions to the image data deriving from a certain scan plan.

The aforesaid unit defining one or more ROIs communicates with the processing unit for verifying the scan plan and/or determining and/or selecting the contributions to the image data deriving from a certain scan plan, and provides to the same the pixels or voxels of the image parts that correspond to said ROIs for the execution of verification activities and for the execution of determination and selection activities.

Alternatively or in combination with the previous characteristic the system can provide a unit of variation in the sense of a reduction or restoration of the resolution and/or the number of pixels or voxels is provided, which unit communicates with the processing unit of verification of the scan plane and/or of the determination and/or of the selection of the contributions to the image data deriving from a certain scan plane and furnishes to the said processing unit the pixels or voxels of the images having a reduced resolution or the reduced number of pixels or voxels for the execution of verification activities and for the execution of determination and selection activities, while the said unit communicates with the processing unit for the execution of the process of extracting information and/or features from the image data furnishing to the said processing unit image data at the original resolution and/or image data in radio frequency format.

In both embodiments and in any of the corresponding variants and/or improvements, different types of machine learning algorithms can be used, such as for example classifiers, neural networks, genetic algorithms and other similar algorithms.

These and other characteristics and advantages of the present invention will become apparent from the following description of some embodiments shown in the attached drawings:

FIG. 5 shows a typical diametric/biparietal scan plane for skull diameter measurement and the list of anatomical markers that define this plane.

FIG. 6 shows, similarly to FIG. 5, an example of the trans-ventricular scan plane and the list of anatomical markers that define this scan plane.

FIG. 19 shows a table containing some examples of classes of acquired images and the measurements that can be made on these images.

With reference to the figures, these show some embodiments of the method and of a system for implementing the same, and said examples are not to be considered as limiting the more general protective scope.

In particular, as will be further specified in relation to the various embodiments, the method according to the present invention provides two embodiments one specifically for determining a scan plane during scanning by means of a 2D probe and the other for determining the scan plane by means of a 3D probe.

The correct determination of the scan plane may have different purposes depending on the field of use, i.e. the type of subject and the type of information that one wishes to extract from the image data.

Although the following examples are applied to the field of obstetrics, i.e. to foetal imaging for the extraction from the images of dimensional data functional to the verification of the correct formation of the foetus, the invention is not limited to this application and can also be extended to other subjects and other characteristics to be extracted from the ultrasound images of anatomical targets of the subject.

Furthermore, with the term image data, the present description generally refers to both the RF signals generated by the ultrasonic transducers on the basis of the received reflection signals, or to the contributions of said signals after the receiving beamforming process, or to the contributions of the radio frequency (RF) signals resulting from the various reflectors within the body under examination, and to the values characterising the pixels or voxels of an ultrasound image generated by said contributions of radio frequency signals.

Figure 1:
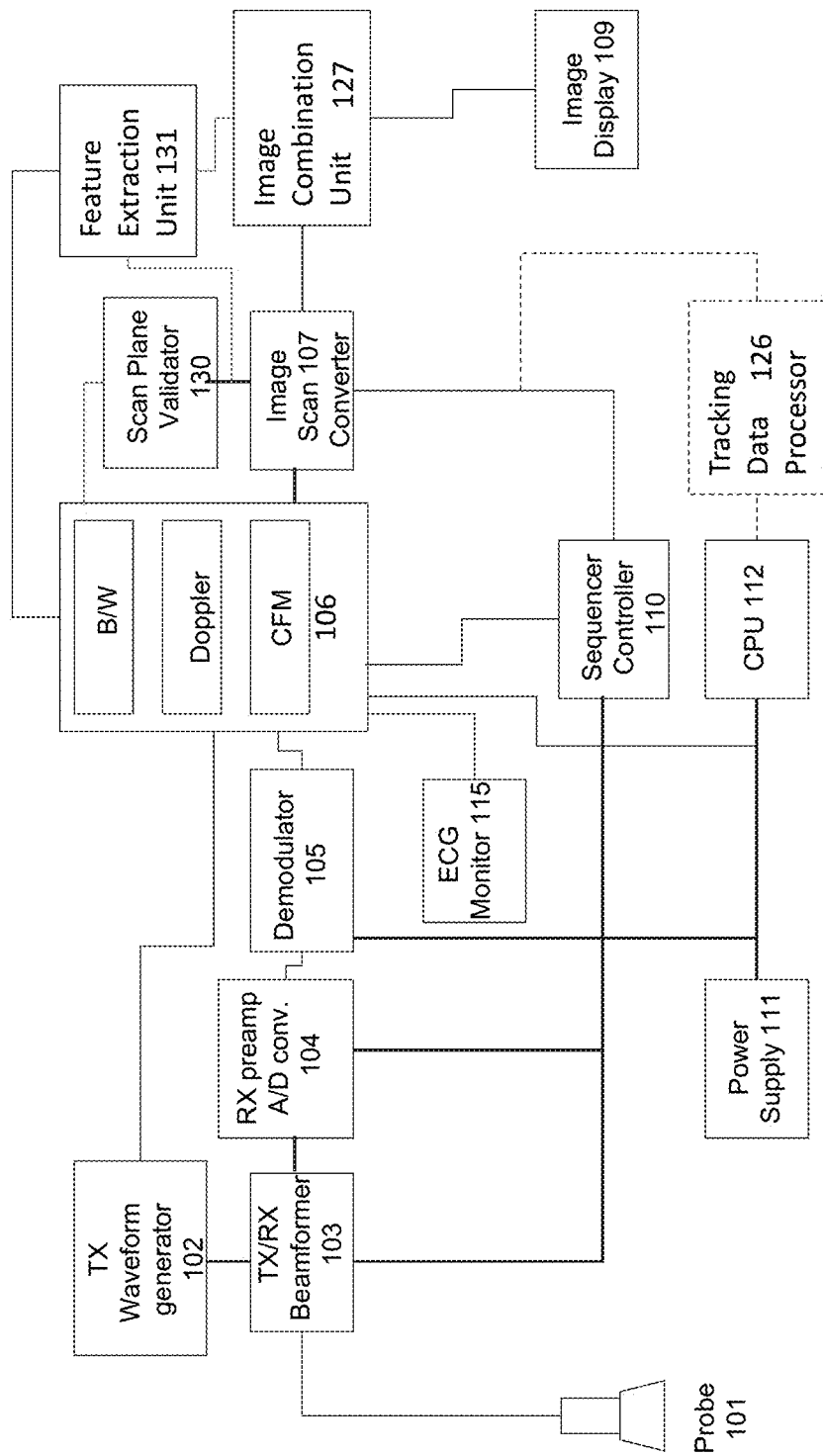
FIG. 1 shows a high-level block diagram of an embodiment of an ultrasound imaging system according to the present invention.

With reference to FIG. 1, the figure shows a high-level diagram of an embodiment of an ultrasonic system according to the present invention.

The probe 101 may include different configurations of transducer arrays, such as a one-dimensional array, a two-dimensional array, a linear array, a convex array, and the like. The array transducers can be managed as a 1D array, 1.25D array, 1.5D array, 1.75D array, 2D array, 3D array, 4D array, etc.

The ultrasound probe 101 is coupled through a wired or wireless connection to a beamformer 103. The beamformer 103 includes a transmitting beamformer (TX) and a receiving beamformer (RX) which are represented together by the TX/RX beamformer 103. The TX and RX parts of the beamformer may be implemented together or separately. The beamformer 103 provides transmission signals to the probe 101 and performs the beamforming of the "echo" reception signals received from the probe 101.

A TX waveform generator 102 is coupled to the beamformer 103 and generates the transmit signals that are supplied by the beamformer 103 to the probe 101. The transmit signals may represent various types of ultrasonic TX signals, such as those used in connection with B-mode imaging, Doppler imaging, colour Doppler imaging, pulse inversion transmission techniques, contrast-based imaging, M-mode imaging and the like. In addition or in alternative, the transmit signals may include single or multi-line transmission, transmit pulses may be focused on single lines or may be focused in such a way as to insonify, larger areas or the entire ROI in the form of plane waves.

The beamformer 103 performs beamforming on received echo signals to form beamformed echo signals in connection with the positions of pixels distributed in the region of interest. For example, in accordance with certain embodiments, transducer elements generate raw analogue reception signals that are provided to the beamformer. The beamformer adjusts delays in order to focus the reception signal along one or more selected receive beams and at one or more selected depths within the region of interest (ROI). The beamformer adjusts the weighting of the reception signals to achieve the desired apodization and profile. The beamformer applies weights and delays to the reception signals of the single transducers that correspond to the probe. The delayed and weighted reception signals are then summed to form a coherent reception signal.

The beamformer 103 includes (or is coupled to) a preamplifier and/or A/D converter 104 that digitizes the reception signals at a selected sampling rate. The digitalisation process may be performed before or after the summing operation that produces the coherent reception signals. The beamformer also includes (or is coupled to) a demodulator 105 that demodulates the reception signals to remove the carrier waveform. Once the reception signals are demodulated and digitized, complex reception signals including I,Q components (also referred to as I,Q data pairs) are generated. The I,Q data pairs are saved in a memory as image pixels. The I,Q data pairs define the image pixels for the corresponding individual positions along the corresponding lines of sight (LOS) or sight lines. A collection of image pixels (e.g. I,Q data pairs) are collected over time and saved as 2D frames and/or 3D volumes of image data. The image pixels correspond to the tissues and other anatomical features within the ROI.

Optionally, a dedicated sequence/timing controller 110 may be programmed to manage the timing of the acquisition, which may be generalised as a sequence of shots intended to select reflection points/targets in the ROI. The sequence controller 110 manages the operation of the TX/RX beamformer 103 in connection with the transmission of ultrasonic beams and the measurement of image pixels at individual LOS positions along the lines of sight. The sequence controller 110 also manages the collection of reception signals.

One or more processors 106 and/or CPUs 112 perform various processing operations as described herein.

For example, the processor 106 executes a B/W module to generate B-mode images. The processor 106 and/or CPU 112 executes a Doppler module to generate Doppler images. The processor executes a color flow module (CFM) to generate colored images. The processor 106 and/or CPU 112 may implement additional ultrasonic imaging and measurement operations. Optionally, the processor 106 and/or the CPU 112 may filter the first and second displacements to eliminate motion-related artifacts.

An image scanning converter 107 performs the scanning conversion of image pixels to convert the image pixel format from the coordinate system of the ultrasound acquisition signal path (e.g., the beamformer, etc.) and from the coordinate system of the display. For example, the scan converter 107 can convert image pixels from polar coordinates to Cartesian coordinates for frames.

A kinetic memory not illustrated in detail stores a collection of frames over time. The frames may be stored with formats in polar coordinates, Cartesian coordinates, or other coordinate system.

An image display 109 displays various ultrasound information, such as frames and information measured according to the embodiments herein. The image display 109 displays the ultrasound image with the region of interest indicated.

A control CPU module 112 is configured to perform various tasks such as user/interface implementation and general system configuration/control. In case of all-software implementation of the ultrasound signal path, the processing node usually also contains the functions of the control CPU.

A supply circuit 111 is provided to supply the various circuits, modules, processors, memory components and the like. The power supply 111 may be an AC power source and/or a battery power source (e.g., in connection with a portable function).

According to the present embodiment and by way of example, the processor 106 may be associated with or possibly also comprise an ECG monitoring module that receives signals from an ECG (not shown in detail) and enables to combine image acquisition with ECG signals according to different variants of known techniques of image acquisition synchronised by ECG signal.

With reference to the present invention, in relation to a first embodiment in which the probe is a probe able to acquire two-dimensional (2D) scanning images, the system comprises a validation processor of the scan plane indicated by 130. As will be explained in more detail below, the said validation processor of the scan plane along which an image has been acquired verifies whether the acquired image is coincident with the optimal scan plane with respect to the body under examination in order to perform feature extractions from said image. This operation can be carried out in different ways, for example by means of a machine learning algorithm.

The image data of the acquired image along the scan plane validated by the validation processor 130 are delivered to a feature extraction processor which is indicated by 131 in FIG. 1.

The results of feature extraction from the acquired image may be combined with the image itself and displayed either superimposed or side-by-side on a monitor 109 by means of an image combination module denoted 127.

With reference to the processing processes of feature extraction, these processes may be intended for different purposes. As will be shown in more detail in the following description, image data, whether in radio frequency format or that relating to image pixel or voxel features, can be used to determine measurements of anatomical and/or morphological details. Alternatively, or in combination, processing of feature extraction may also be related to the identification of the quality or typology of tissues represented in the image, such as in the identification of tumours and whether they are benign or malignant, or in the identification of other tissue characteristics.

Although the modules 130 and 131 are shown as separate modules provided with inputs and outputs of the data to be processed and of the data produced by the corresponding processing, these modules may also be integrated into the processor 106 and/or the CPU 112 or divided over both so as to divide the computational burden over several processors operating in parallel.

The aforementioned integration may also be at least partially implemented at the hardware level. However, since generally said modules 130 and 131 are implemented in the form of a hardware comprising a generic processing unit in which is loaded a program that encodes instructions to make said generic hardware to perform operations related to validation of the scanning plan and/or extraction of features, and which hardware executes said program, the preferred integration takes place at software level being the said program or programs loaded and executed by the processor 106 and/or the CPU 112.

On the other hand, with respect to a second embodiment, which comprises the acquisition of a three-dimensional image of a region of interest, the definition of a scan plane intersecting said volume and having a position and orientation with respect to said volume that are corresponding to the optimal scan plane for the extraction of features and the selection from the set of image data related to the volumetric image of contributions that fall within or are coincident with an intersection plane of said volumetric image, a further module 126 for tracing the position of a sequence of two-dimensional scan planes in which the scan planes are displaced relative to each other so as to cover a volume of the target object is shown with dotted lines in FIG. 1.

In this case, the modules 130 and 131 operate for the definition of the scan plane, i.e. the plane of intersection of the volumetric image coinciding with the desired scan plane and for the selection of the image data falling on said plane, as well as for the processing related to the extraction of the features. In this case, said modules 130 and 131 execute a processing software in which instructions are encoded for selecting the position and orientation of the scan plane and for defining the intersection plane of the volumetric image that corresponds to said scan plane, as well as for selecting image data coinciding with said plane and for the processing of extraction of desired features.

It is worth mentioning here that the specified module 126 is only an example of a volumetric image acquisition unit that is generally coupled to a probe able to acquire two-dimensional images, whereby the 3D image is acquired by combining the two-dimensional images acquired along a plurality of adjacent scan planes in a common reference system.

The different scan planes can be offset according to a translation direction perpendicular to themselves and parallel to each other, or the scan planes can be angularly offset to each other, having a succession of angles with respect to a common oscillation axis. An alternative embodiment may include the acquisition of a volumetric image of a target region by means of a probe of the type having a two-dimensional transducer array or capable of acquiring three-dimensional images without requiring probe displacement relative to the patient and probe tracking systems.

The modules 130 and 131 of FIG. 1 are shown as modules integrated in the ultrasound system, but may also be separate from the same and form part of at least one separate processing unit performing the functions of said modules 130 and 131.

Figure 2:
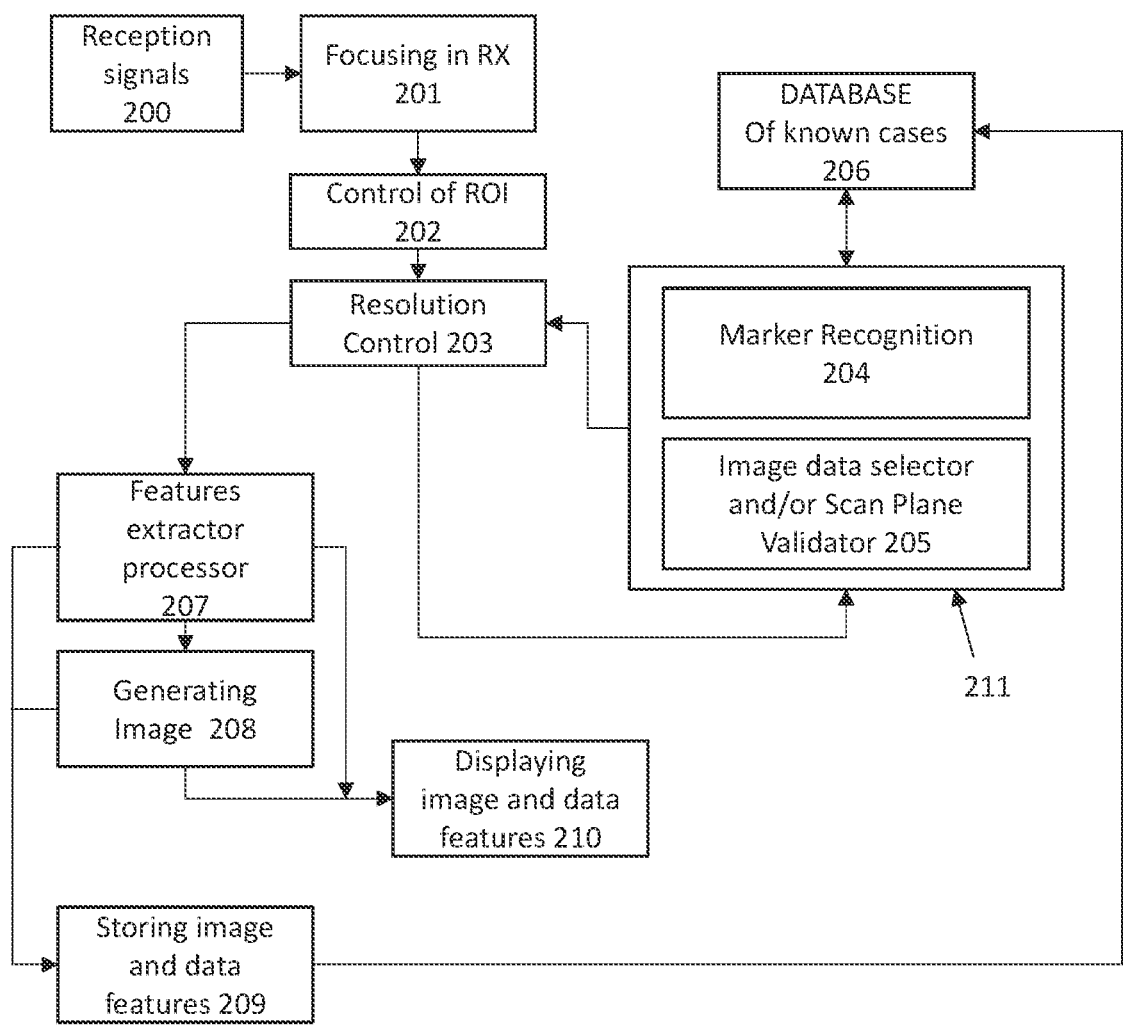
FIG. 2 shows a block diagram of an embodiment of a receiving signal processing unit for determining the scan plane and extracting features from image data.

Regardless of the embodiments and variants, the block diagram of FIG. 2 shows an embodiment of a processing system constituting an embodiment in which the modules 130 and 131 related to the scan plan validator and the feature extraction processor are integrated.

200 indicates an input to the system for reception signals and this module is part of the ultrasound system and is only shown for a better understanding of the data streams. The reception signals are processed by the receive beamformers for extraction of the contributions of the reception signals derived from the acoustic wave reflection points within the area where the transmission beam was transmitted. The focusing 201 takes place according to one of several possible variants known and used in the various existing ultrasound systems. The set of RF signal contributions is then ordered in a manner corresponding to the position of the reflectors within the area where the ultrasonic beam was transmitted.

The spatial or topological order of the reception signal contributions derived from the individual reflectors along a two-dimensional plane or a three-dimensional volume corresponds to the order of the pixels or voxels of the final image, wherein the aspect of said pixels or voxels being a function of parameters derived from said signal contributions.

A control section of the region of interest referred to as ROI and indicated with 202 allows to delimit the acquired and sorted data to one or more specific regions of the data set corresponding to the various signal contributions, which in this document are also referred to as radio frequency image data or raw image data.

Such one or more ROIs may have greater or lesser extents as chosen by the user and/or also different positions within the image.

Regarding the embodiment in which a two-dimensional image is acquired along a scan plane and the scan plane verifier performs a verification of coincidence of said scan plane with the position and/or orientation of the optimal scan plane for performing feature extraction processing, it is possible that the position and orientation of the scan plane along which the ultrasound image was acquired are verified by specific anatomical markers that must all be present simultaneously on the image related to the scan plane along which it was acquired. In this case, such anatomical structures acting as markers, may have limited extensions with respect to the dimensional size of the whole image and/or also different positions in the image itself, one with respect to the other.

According to an embodiment of the present method and of the system for its implementation, the processing unit that verifies the scanning plan and performs the extraction of features from the image data can be provided with a control module of the ROI indicated with 203, thanks to which it is possible to set one or more ROIs with respect to their position and extension which contain at least a part of the aforementioned anatomical marker structures.

The definition of the position and/or size of the ROIs can be set manually by the user or it can be set by an automatic process.

In the case of a manual setting, the processing system may comprise a user interface with input devices such as keyboards, touch screen systems or traditional point-and-click devices.

With the variant of automatic setting, it is possible to perform, by means of an image processing software configured for the recognition of objects in the image, the recognition, at least approximate, of the structures constituting the anatomical marker or markers and then to provide for the positioning of a corresponding ROI for each identified anatomical structure or an ROI containing at least a part of said anatomical structures, by sizing at the same time said ROIs so as to contain at least the major or most characterizing part of said anatomical structures with reference to the functional features for the automatic recognition thereof.

A great number of software for recognising objects in images are known in the state of the art. These include, for example, facial recognition algorithms, pattern recognition algorithms and also classifiers. This list is not exhaustive, but merely illustrative.

In relation to and in combination with the ROI definition step, it is possible to provide a resolution control section, which is indicated by 203 in the system example of FIG. 2. This section can operate independently of the ROI control section and can also be used to reduce the number of image data to be processed in the step of automatic ROI definition for performing the approximate recognition of marking structures.

The reduction of the number of image data can be achieved, for example, by reducing the resolution of the image data, for example, by fusing together a predetermined number of image data related to adjacent positions in the said topological distribution of the image data. When the term image data refers to the pixels of an image, the said fusion operation may advantageous comprise the summation, possibly even weighted, of the intensities of a certain number of adjacent pixels to form a single pixel.

An alternative way of reducing the number of image data can be, for example, a simple decimation of the image data and therefore the elimination of a certain number of image data.

Generally, it is advantageous to carry out a first step of reduction of the number of image data according to one or more of the previous alternatives, to define the ROI or ROIs relative to the anatomical marking structures of interest and then to transform only the image data present in the said ROIs into an image, that is, into a set of pixels or voxels present in the said ROI or ROIs.

This generates two- or three-dimensional images that have a reduced number of pixels or voxels compared to the entire image, as they are limited only to one o more ROIs. These image data are then supplied to a verification section of the scan plane along which the image was acquired. Said scan plane verification section is globally indicated with 211.

Depending on whether the system operates according to a first of the two alternative embodiments of the method, i.e. the embodiment that foresees the acquisition of two-dimensional images, or according to the second embodiment, i.e. the embodiment that foresees the acquisition of a three-dimensional image, the verification section of the scan plane operates in two different ways.

In the first case, it is verified whether in the ROIs are represented in an optimal way the anatomical marking structures in order to guarantee that the scan plane coincides with the predetermined scan plane that is optimal for the execution of feature extraction.

This is highlighted by the module 204 which performs a recognition of anatomical marker structures, i.e. briefly anatomical markers, and by the module 205 which compares the image data, i.e. the pixels or voxels related to the marker structures identified in the acquired image with those of known cases which are saved in the records of a database of known cases indicated by 206.

In the second case, since a volume is acquired, the section 211 always operates by recognising the marking anatomical structures within the volumetric image and then defining a predetermined optimal scan plane for feature extraction.

In this case, once an intersection plane of the volumetric image has been established that corresponds to the predetermined optimal scan plane for performing feature extraction, the section 211 proceeds to construct the image by selecting the contributions of the image data that fall along said section plane. In this way, a two-dimensional image is generated that corresponds to an image acquired by two-dimensional scanning along an optimal scan plane for feature extraction.

According to whether it is the variant where a two-dimensional image is acquired or the variant where a three-dimensional image is acquired, the contributions of the image data that fall on the verified or reconstructed scan plane are used for the feature extraction from the data.

According to an embodiment, this process can be carried using image data in RF format, i.e. raw data before conversion into pixels or voxels. Thanks to this variant, it is possible to have a greater quantity of information available and therefore to obtain a better result in relation to the extraction of the searched features.

The extraction step is performed by an extraction processing module indicated with 207, in this case the result may be an image and/or numeric or alphanumeric data which may then be displayed together on a display 210 after the image is generated in the module 208.

According to the system of FIG. 2, the recognition of the anatomical marking structures and/or the verification of the scan plane are performed by means of a machine learning algorithm which is trained on the basis of the information saved in the database of known cases.

The machine learning algorithm can be selected from a plurality of algorithms and can also comprise a combination of these algorithms.

Examples of algorithms can be predictive algorithms, classifiers such as neural networks or even genetic algorithms.

In this case as illustrated in FIG. 2, the image data relating to the feature extraction and to the generation of the corresponding image along the optimized and predetermined scan plane are stored in the database in combination with the extracted features as indicated by 209.

Figure 3:
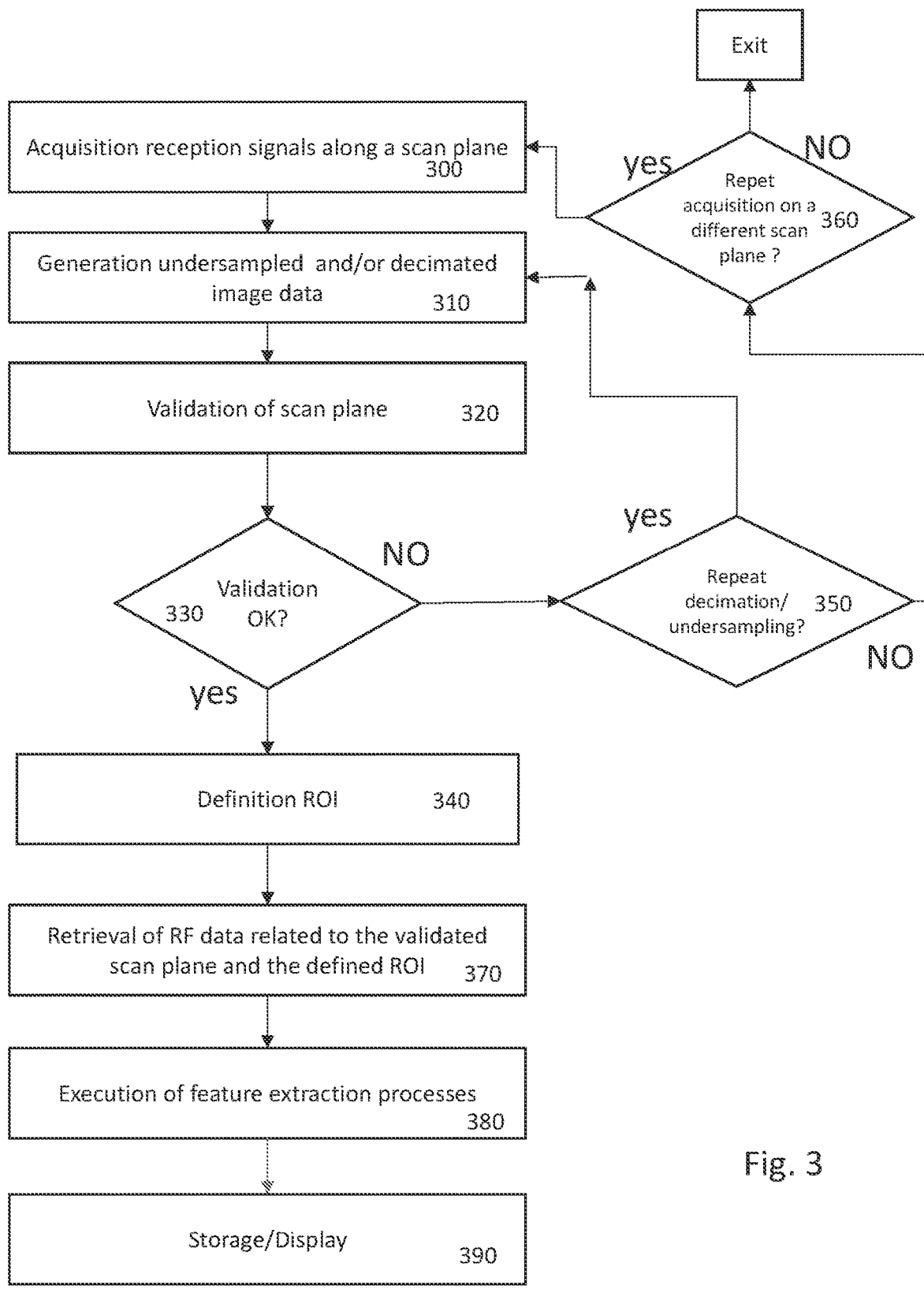
FIG. 3 is a block diagram of steps of an embodiment of the process for determining the scan plane and extracting features from the corresponding image data according to an embodiment of the present invention.

FIG. 3 shows a flowchart of the method according to the first embodiment of the present invention comprising the acquisition of two-dimensional images.

At step 300, acquisition by means of an ultrasound system is shown, for example a system according to FIG. 1 of reception signals along a scan plane that pass through the body under examination and along which ultrasound transmission beams are transmitted.

From these receiving signals, which are in the form of radio frequency signals, digital images are generated by means of a scan-converter. These are preferably under-sampled to reduce the amount of data to be processed in the subsequent steps as indicated in step 310. Instead of an under-sampling and/or in combination with the same, it is possible to carry out a decimation and/or a reduction of resolution of the images or other elaborations in order to reduce the amount of data to be processed so as to make the activities of the validation steps of the scan plan less onerous.

At step 320, the validation of the scan plane is performed with respect to the position and/or orientation of said scan plane.

As already previously described in the introductory part of the present description, said validation takes place by using algorithms for calculating the similarity of the acquired image with the images of a database of known cases and in which are memorized the ultrasound images whose scan plane is considered suitable and/or optimal for the extraction of the desired features from the image data.

Several operating modes are possible. According to an embodiment, to this end, machine learning algorithms are used which are trained to identify whether or not the scan plane of the image to be validated is the suitable and/or optimal one for the extraction of the desired features from said image, on the basis of the image data, possibly also undersampled and/or decimated and possibly also in relation to ROIs of reduced size as indicated in step 310 corresponding to what has been performed for the image data related to the image acquired and to be validated.

Said machine learning algorithms can be in the form of classifiers or comparators and/or may operate according to different principles such as, for example, being structured as neural networks, correlation algorithms, genetic algorithms and other types of algorithms or combinations thereof.

If the result of the validation is positive, as indicated in step 330, ROIs are defined in the image which are coincident with one or more regions of said image and/or of the data space of the image, in which the informations to extract the searched features are present as indicated in step 340.

Then at step 370, the radiofrequency image data that are relative to the validated acquisition plan are retrieved for the aforementioned ROIs In this way, at the next step 380 of executing the process of extracting the features, i.e. the searched features, the most complete data acquired during the scanning and containing the greatest amount of information is provided.

At step 390, the identified features and/or the corresponding images are memorized and also displayed and depending on the type of description of these features, the display may take place either in graphic or alphanumeric mode.

When as indicated in step 330 the validation result of the scan plane of the acquired image is negative, it is allowed to choose between two repetition alternatives as indicated in step 350. A first alternative consists in performing an alternative step of reducing the weight of the data used for the validation, as for example described with reference to step 320.

This repetition of the step 320 can occur with parameters for reducing the weight of the image data, such as for example the under-sampling and/or the decimation and/or the choice of one or more ROIs and then the validation process is repeated.

Alternatively, as indicated in step 360, it is possible to choose whether to terminate the process or to repeat the acquisition of an image, which can be done by modifying the position of the probe with respect to the object under examination so as to modify the scan plane along which said image is acquired.

In this case, as already shown, step 360 leads to the initial step 300 and the entire flow described can be repeated.

In an embodiment, it is possible to provide for further alternatives which can be performed in case of non-validation at step 330 and which can be applied together or in sequence if the repetition step does not also lead to a positive validation outcome.

For example, in a first repetition step of the process after a negative validation outcome it is possible to repeat only step 310 according to one or more of the variant embodiments described above.

At the same time, it is also possible to vary the algorithm used for validation and/or to set parameters for the setting of said algorithm.

Alternatively, this step of modifying the validation algorithm and/or the settings thereof, can be performed if the validation step 330 is performed on image data obtained from a first repetition of the reduction steps of the data weight according to one or more of the variants described with reference to step 310, while the acquisition of the image according to step 300 can only be repeated after the validation has given a negative outcome also as a result of a repetition of the process with a different algorithm or with a modified setting of said algorithm.

The order of the sequence of the repetition of the steps 310 and/or 300 and/or the modification of the validation algorithm and/or the settings thereof, may be any and not limited to the foregoing.

Still an embodiment can provide in combination with the foregoing a maximum value of repetitions of the validation process.

In this case, a variant embodiment can provide for a number of maximum possible repetitions.

In combination or in alternative it is possible to fix an error margin of correspondence of the scan plane of the acquired image with the scan plane foreseen as suitable or optimal for the feature extraction process, the steps of the said repetition being terminated when the validation indicates that a correspondence is present within the said margins.

According to yet another feature, it is also possible to allow the user to modify the said margins using the input interfaces as provided in the embodiment described above.

Figure 4:
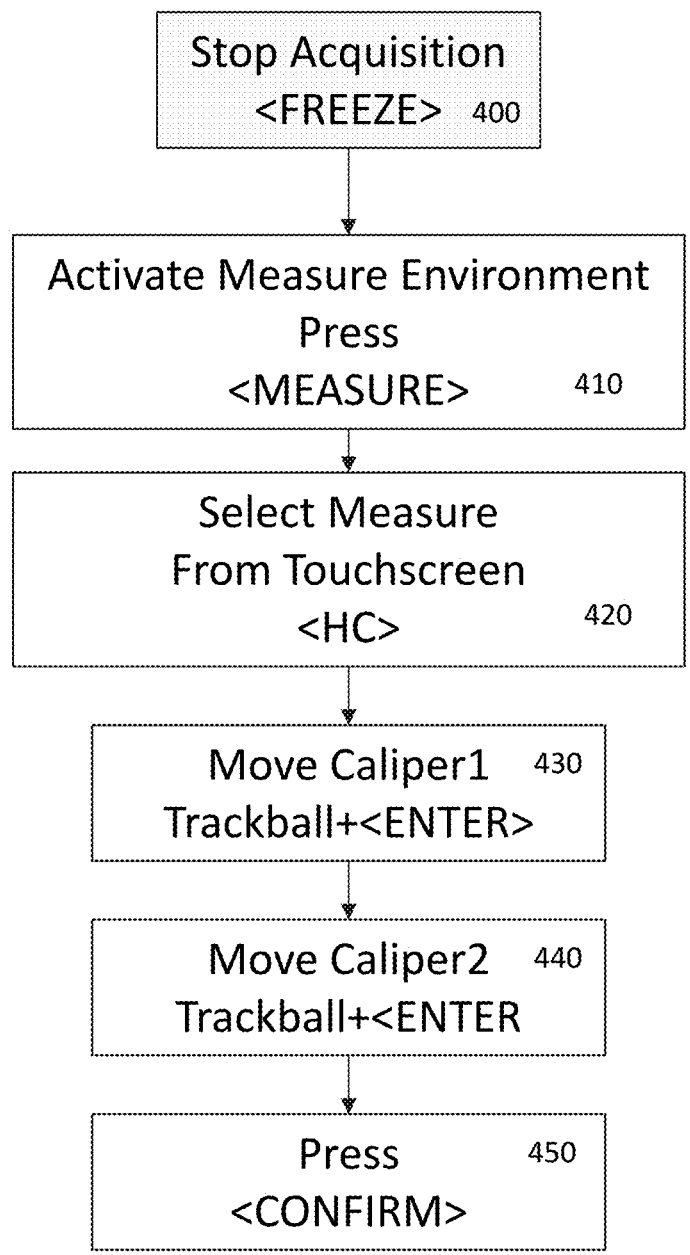
FIG. 4 shows the sequence of manual commands of an example of the process for measuring the skull diameter of an ultrasound image of the foetus.
Figure 7:
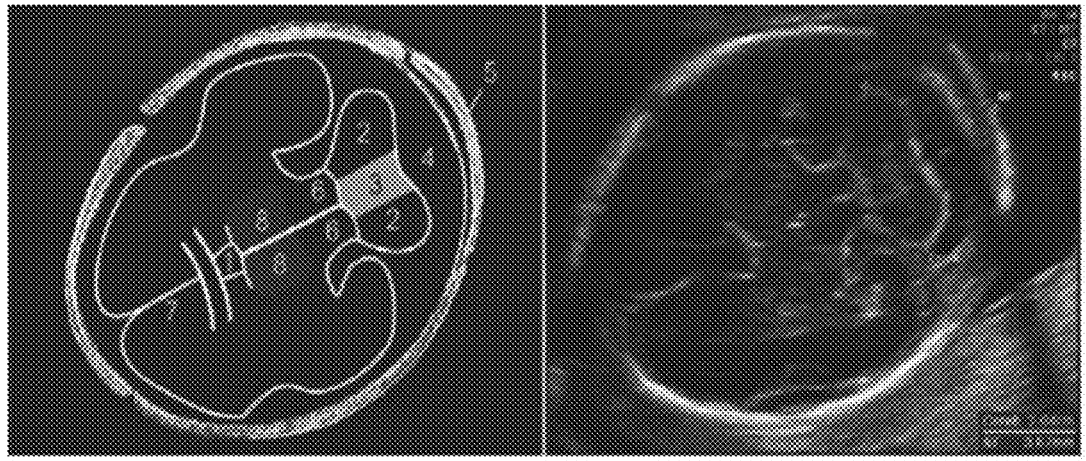
FIG. 7 shows, similarly to the previous figures, the cerebellar scan plane and the anatomical markers defining said plane.

FIG. 4 in combination with the figures shown illustrates an example of feature extraction from images of typical scan planes in the foetal context illustrated in FIGS. 5 to 7 and in which anatomical markers are indicated to identify that the scan plane along which the image is acquired is correct and suitable for extracting the searched features.

In particular, FIG. 5 shows the image suitable for measuring the diameter of the foetal skull. This is identified by a starting point referred to as caliper 1 and the end point is referred to as caliper 2.

The process is shown in the flow chart in FIG. 4. Using one or more of the input interfaces available to the user of the ultrasound system, once the validation of the scan plane has occurred positively, in an embodiment comprising an extraction partly manual and partly automatic of the feature relating to the skull diameter, the user stops the image at step 400. In the next step 410, the measurement process, i.e. the extraction of features, is started.

It is possible that different types of features are extractable and that the user is given the option of selecting a type of measurement and starting the procedure for performing this measurement as indicated in step 420. In this case, the user interface is of the touchscreen type, but it is possible to provide one or more additional input and/or selection devices that can be used alternatively or in combination depending on the user's preference.

For the diameter measurement as shown in FIG. 5, the user drags a first indicator of the start point of the distance measurement indicated with caliper 1 to the position shown in FIG. 5 and as indicated in step 430. In step 440 a second indicator called caliper 2 is placed on the image in the position selected by the user that defines the end point of the length measurement. This is indicated by the dotted line connecting the two symbols that define caliper 1 and caliper 2. In step 450, once the positions of the calipers have been verified, the user gives confirmation and the system calculates the distance on the basis of the image data.

The mode of performing this calculation based on the image data is known to the technician of this branch and can be performed according to one or more of the known technical methods.

The process described above is performed manually with regard to the position of the start and end points of the portion whose length is measured.

According to an alternative embodiment, it is possible to perform the measurement in a fully automated manner using a machine learning algorithm or other algorithms operating on the basis of geometric/analytical or feature recognition in the images or combinations of these algorithms to identify the start and end points of the distance to be measured.

The embodiment illustrated should not be considered to be limitative, as well as the examples of scan planes in FIGS. 5 to 7.

The present invention can be used in many other application fields with regards to performing the feature extraction from diagnostic images. These features may also be different from the determination of measurements, such as the recognition of the quality of identified tissues and/or the identification of blood flows and/or the presence of structures in certain anatomical regions.

According to FIG. 5, the correct plane for the measurement of skull circumference and biparietal diameter must include the anatomical structures related to the cavum septum pellucidum, the thalamus and the choroid plexus in the atrium of the lateral ventricle.

FIG. 6 indicates the main anatomical structures that characterise the transverse plane.

FIG. 7 shows the main anatomical structures that characterise the cerebellar plane.

Figure 8:
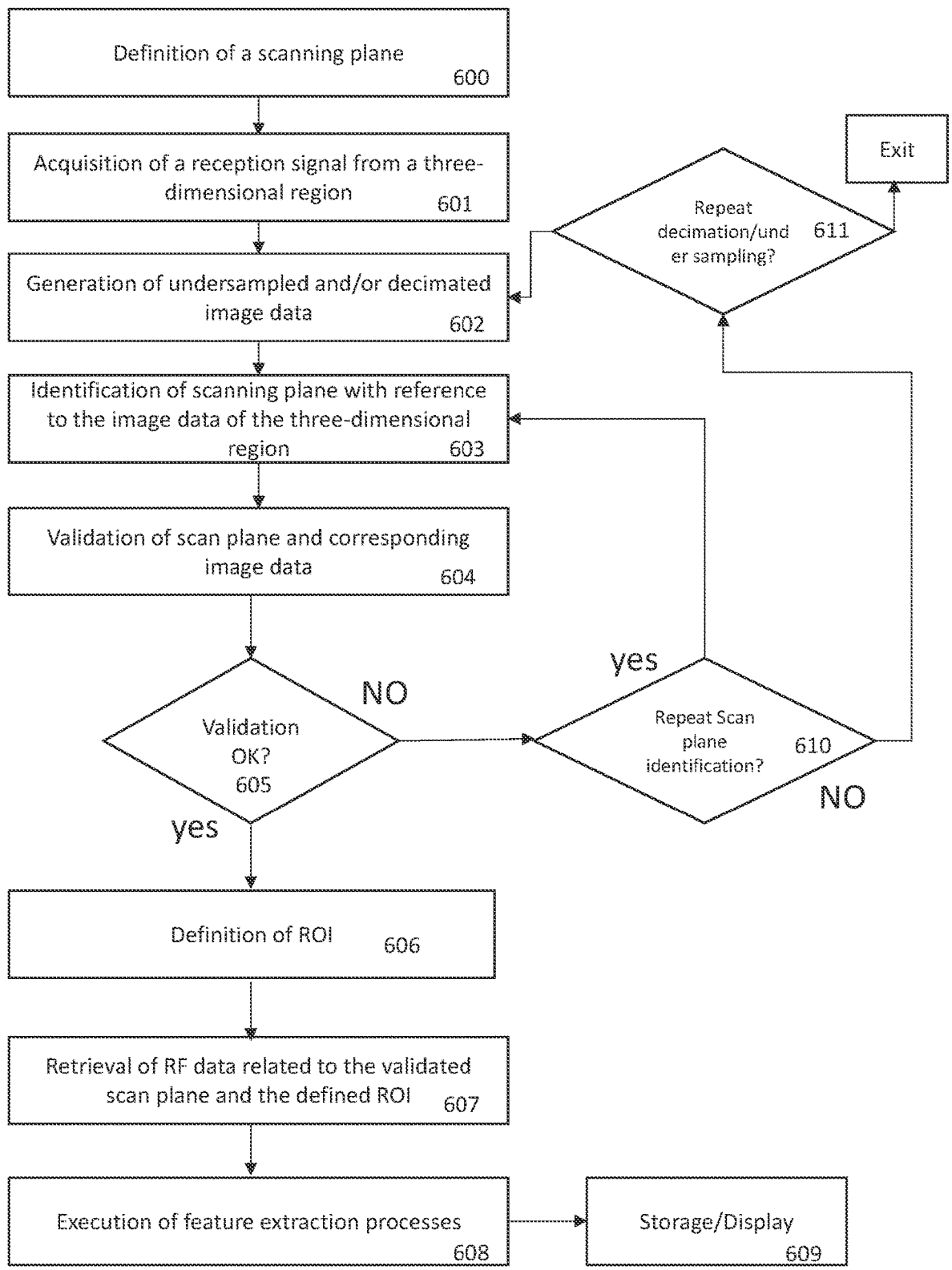
FIG. 8 shows a flow chart according to a further embodiment of the method of the present invention.

FIG. 8 shows the flowchart of the process of determining the scan plane according to a further embodiment of the invention.

This embodiment is particularly suitable in combination with an ultrasound system configured for three-dimensional image acquisition.

The acquisition of three-dimensional ultrasound images also referred to as volumetric images can take place with different types of systems.

According to an embodiment, the ultrasound system is provided with a probe of a type suitable for acquiring two-dimensional images in combination with a system for tracking the movement of said probe along a predetermined direction and/or a predetermined path and which tracking system detects the position and orientation of said probe at the time of acquiring images along adjacent or angularly offset scan planes. The combination of the image data along the individual scan planes by means of detecting the relative position of said scan planes allows the reconstruction of an image of a volume.

In an alternative, the probe is of the type comprising a set of two-dimensional transducers, i.e., distributed in a pattern that extends along a plane or surface in two directions perpendicular to the axis of propagation of the ultrasound beams. In this case, the acquired image covers or extends over a pyramidal or truncopyramidal slice of the body under examination and therefore relates to the part of said organ falling within said slice.

Other solutions are for example motorised probes in which a linear transducer assembly is mounted swaying around an axis parallel to the extension of said linear assembly and the angular displacement around said axis is controlled by a motor such as a stepper motor or the like.

Starting from an acquisition of a three-dimensional image and basing on the anatomical markers that must be present in the image along a scan plane suitable and/or optimized to perform extractions of quantitative or qualitative features from said image, it is necessary to proceed by defining said optimal scan plane with respect to position and/or orientation with respect to the body under examination.

Once the features characterizing the scan plane suitable for performing the extraction of the desired features have been defined and according to an embodiment as indicated in step 600, it is acquired a three-dimensional image of a region of the body under examination in which at least one of said anatomical markers and/or preferably all the anatomical markers characterizing the selected scan plane are provided, as indicated in step 601.

In step 602 similar to the embodiment of the process previously described in combination with a two-dimensional image acquisition, the weight of the image data to be used for the execution of the subsequent steps is reduced. This reduction can take place at step 602 for example by sub-sampling said data and/or by decimation and/or also by definition and selection of one or more ROIs which are limited in their position and extent to one or more of the anatomical markers characterising the scan plane.

On the basis of said image data and thanks to the database of known cases, it is possible to identify the position and orientation of the scan plane suitable for feature extraction, relatively to the three-dimensional set of image data that represents the acquired three-dimensional image.

According to an embodiment of the present invention, a machine learning algorithm or a combination of machine learning algorithms such as neural networks, genetic algorithms or other classification and/or prediction algorithms are used among the various possible algorithms.

The process of identifying the scan plane in relation to the acquired three-dimensional image can comprise the steps of identifying the contributions to the image data present in the three-dimensional image and corresponding to the images of the anatomical markers that characterize the scan plane.

Once defined with a certain margin of precision that can be defined and set in advance, the position and orientation of the scan plane is defined with reference to the volumetric image and the set of image data contributions that fall on or coincide with said scan plane is generated.

As indicated in step 604, it is possible to use machine learning algorithms in combination with said database to perform a validation of said scan plane and of image data contributions falling on said scan plane.

If the validation of the Scan Plan is positive, as indicated in step 605 according to the illustrated embodiment, in step 606 an ROI is defined relative to the region of the image data which contains the information to be extracted from said image. Instead, in step 607 the image data relating to said ROI and in the scan plane validated in the previous steps are retrieved, i.e. identified.

Therefore, an image data set is generated which is relative to a two-dimensional image along the validated scan plane.

In an embodiment and similar to the embodiment of the previous example, it is also advantageous in this case to use the image data consisting of the received radio-frequency signals relating to the contributions of the reception signals derived from the validated scan plan. These data, which have not yet been subjected to subsequent steps of conversion into pixels or voxels, are still substantially in the raw state and contain a greater amount of potential information.

On the basis of these data, the extraction of the desired features is then performed according to one of the known techniques and/or using automated systems which can be based on machine learning or other artificial intelligence algorithms, similarly to what has been described with reference to the measurement of the diameter of the skull of the foetus for the preceding embodiment.

The results of such processing as well as the images on which they are based may then be displayed and/or also recorded as indicated in step 609.

Returning to verification step 605, if the validation of the scan plan produces a negative result in the present embodiment, it is possible to repeat the previous steps or terminate the process. A first alternative is indicated in step 610 which provides for the repetition of the identification and validation of the scan plan of step 604. In this case, it is possible for example to modify the settings of the algorithm that performs the identification of the scan plan according to the image data relative to the anatomical markers foreseen for the scan plan and in function of the database of known cases which trains the algorithm. In combination or in alternative, it is also possible to modify the algorithm used or to combine to the algorithm used further algorithms that perform image data optimisation or other pre- or post-processing steps.

Step 610 gives the alternative of also carrying out a repetition of step 602 before carrying out step 603 again. In this case, it is possible to operate on the sampling mode, on the decimation mode or on other reduction modes of the weight of the image data, as well as on the selection of the one or more ROIs containing the anatomical markers of the acquired image. In this way, the dataset that is used for the step 603 is modified and can be subjected to a processing of the step 803 maintaining the same algorithm of the previous step, or the algorithm and/or the settings thereof can also be modified according to one or more of the alternatives described above.

With regard to the possible repetitions also in relation to this embodiment are valid the possible embodiments described with reference to the preceding example embodiment.

In particular, the order of the sequence of the repetition of the steps 603 and/or 602 and/or the modification of the validation algorithm and/or the settings thereof, can be of any kind and is not limited to the foregoing.

Still an embodiment can provide in combination with the foregoing a maximum value of repetitions of the validation process.

In this case, a variant embodiment can provide for a number of maximum possible repetitions.

In combination or in alternative it is possible to fix an error margin of correspondence of the scan plane of the acquired image with the scan plane foreseen as suitable or optimal for the feature extraction process, the steps of the said repetition being terminated when the validation indicates that a correspondence is present within the said margins.

According to yet another feature, it is also possible to allow the user to modify the said margins using the input interfaces as provided in the embodiment described above.

Again similar to the first embodiment of FIG. 3, the extraction of features from the image can occur either manually, in a combined manual and automatic manner or in a fully automatic manner, as described with reference to the non-limiting example of FIGS. 4 to 7.

FIGS. 9 to 14 show a non-limiting, visually comprehensible example of a variant of the method of this second embodiment.

In this case, the example relates to the use of a phased array-sector probe in which a linear transducer array is oscillated about an axis parallel to the longitudinal extension of said transducer array by means of a motor, for example a stepper motor, the angular orientation position of the array being recorded at each acquisition. The activation in transmission and reception of the probe is synchronised with the forward movement in such a way as to cover the volume under examination V with a succession of scanning planes which have different predetermined orientations in space and which are arranged in a fan-like manner as illustrated and indicated with S1, S2, S3 and Sn in FIGS. 9 to 14.

FIGS. 9 to 14 illustrate in a very simplified way the principle on which the method according to the present invention is based, with reference to the use of a probe for three-dimensional acquisitions of the aforementioned type.

Figure 9:
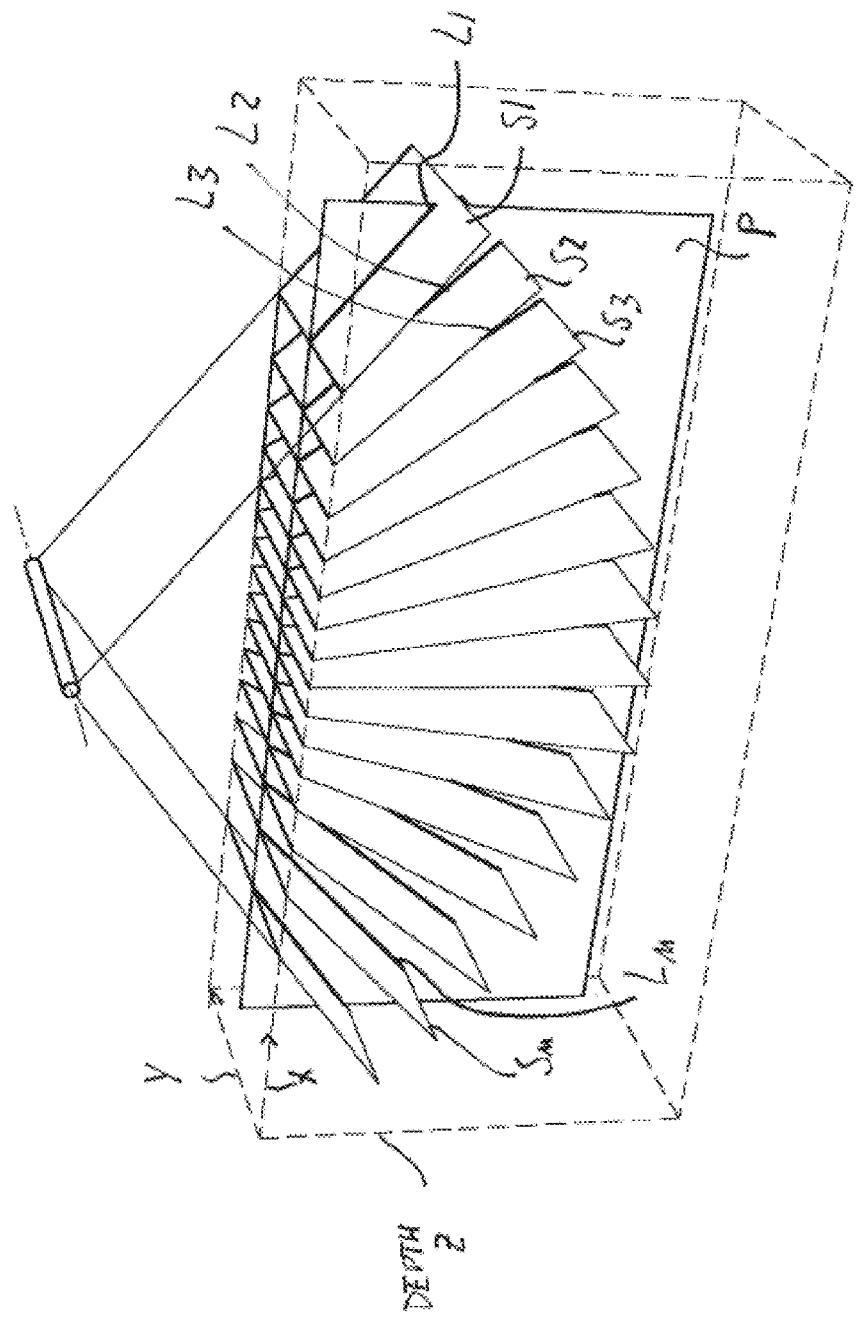
FIGS. 9 to 14 show some schematic examples of the way the image or the related image data is generated respectively along three examples of scan planes having different positions and different orientations relative to a three-dimensional image.
Figure 10:
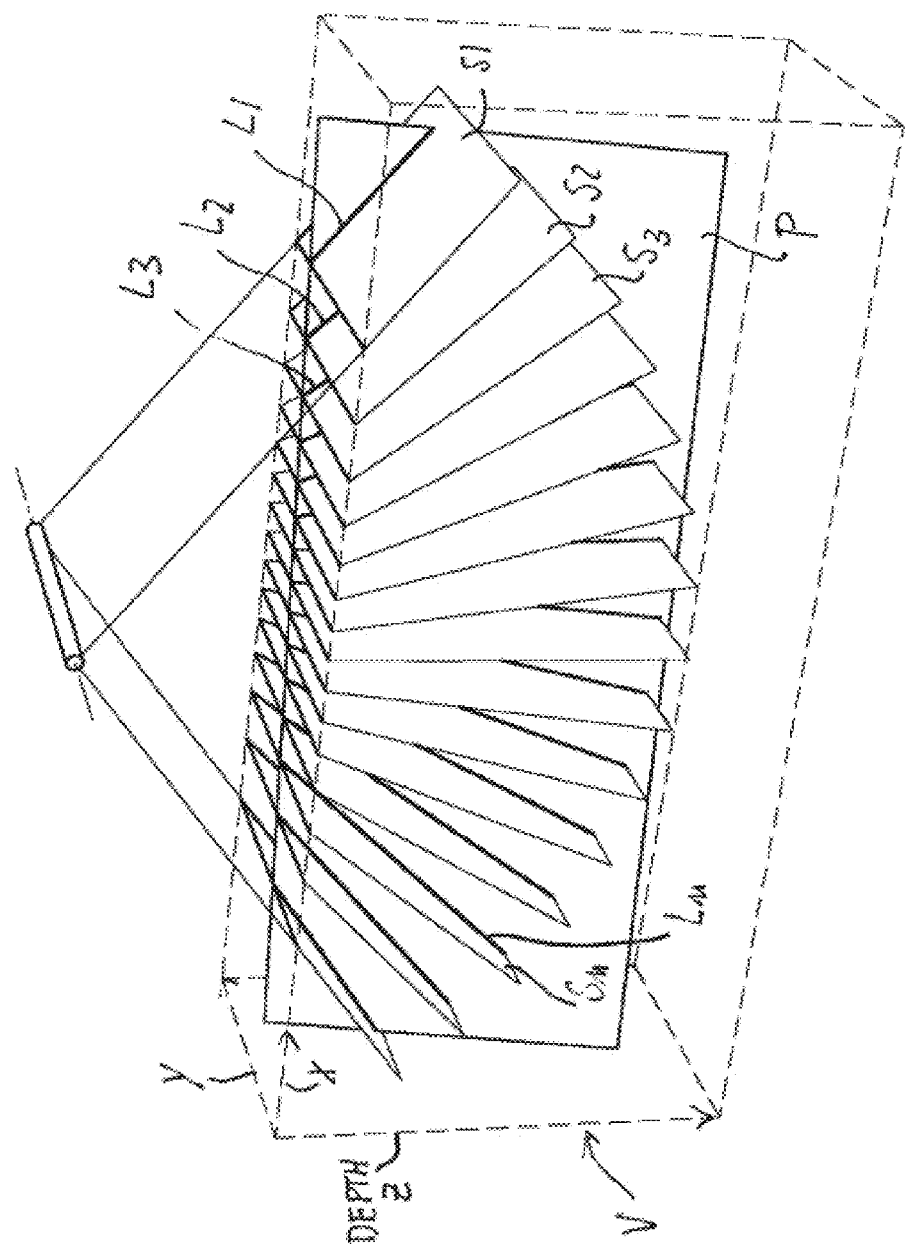
Figure 11:
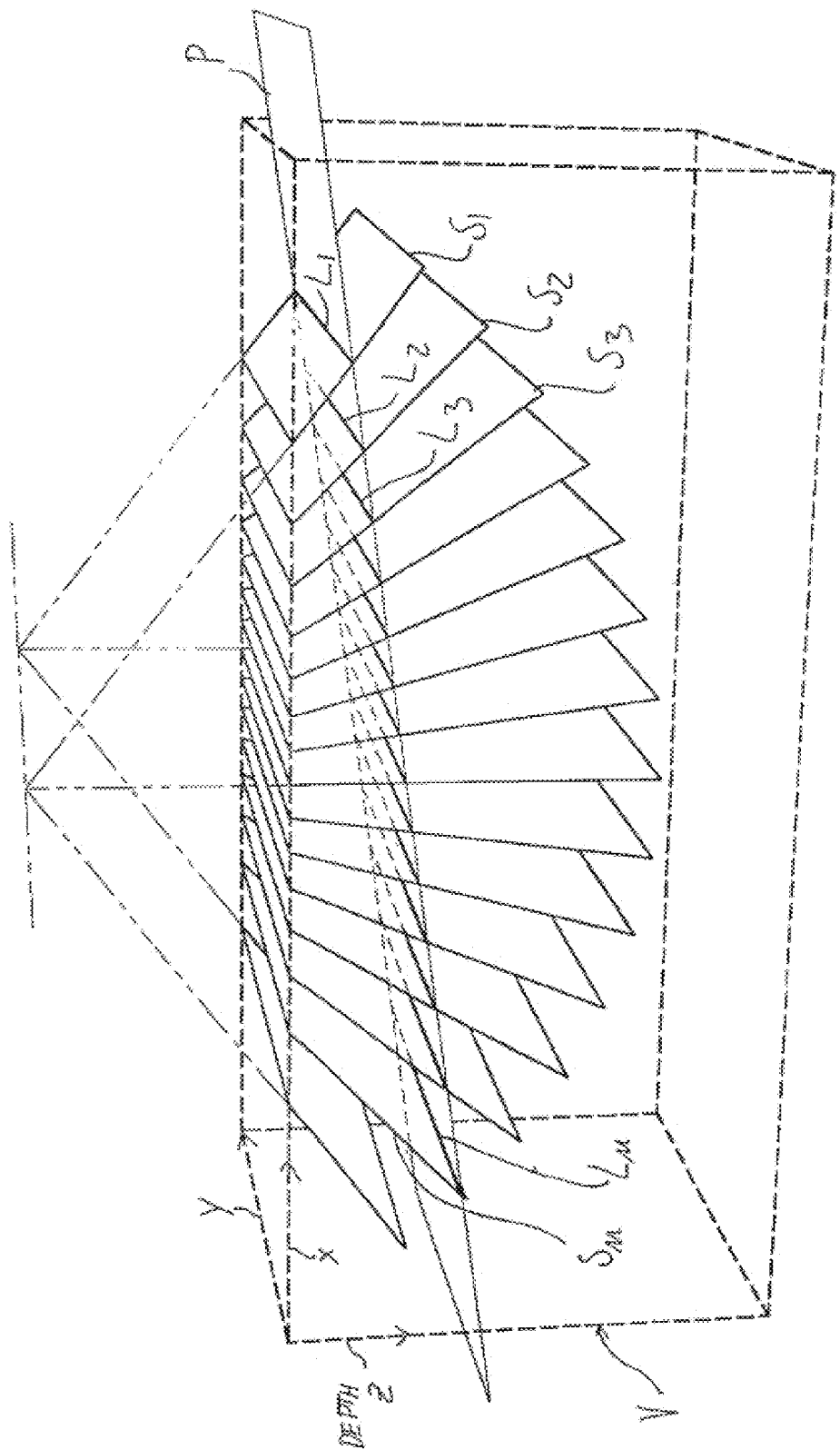

FIGS. 9 to 11 illustrate in principle an embodiment of image reconstruction along a scanning plane intersecting a three-dimensional image, which consists in setting before performing the scanning the orientation and/or position parameters of the section or projection plane or planes of the volume under examination which is to be displayed. Since the positions of the scanning planes S1, S2, S3, Sn are known a priori in relation to a reference scan plane of the probe, the method provides for scanning in the single scanning planes only for the lines that form each scan plane and that coincide or intersect the lines Li, L21 L3, Ln which constitute the intersection lines of the selected display plane or planes with the single scan planes S1, S2, S3, Sn. The positions of these lines in space can be calculated a priori by the main computer, on the basis of the known relative position between the single scan planes and the orientation and position parameters of the plane or planes to be displayed which have been preset by the user.

Therefore, with reference to the present invention it is also possible to make the three-dimensional acquisition of image data faster, for example by reducing the processing chain of the reception signals to a volumetric ROI which contains within it the requested scanning plane and which, however, is a limited region of the entire volume that could otherwise be acquired by means of the probe.

In this case, therefore, the entire volume is not acquired and therefore, the image detection time is drastically reduced, obtaining a considerable acceleration of the image processing that can be truly displayed in real time allowing the service operator to immediately verify whether the acquisition has been performed under the conditions foreseen for the same.

With reference to the examples of FIGS. 9 to 11, different planes P having different orientations are illustrated therein. The most favourable situation is shown in FIG. 9. In this figure, the plane P of the section along which the image is to be taken is perpendicular to the array of scanning planes Sn of the probe. It is clear that in an ideal situation, for each plane it will be necessary to perform the scanning along only one line per plane and that is along the line coinciding with the section lines Ln of the section plane P along which it is wished to detect the image with the scanning planes Sn of the probe. This is evident from FIG. 12 where the scan line is indicated by SCNL.

Figure 13:
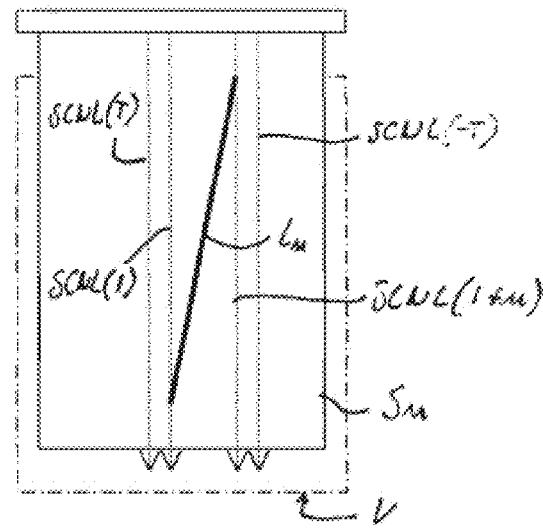

In FIG. 10, the section plane P along which the image is to be detected is inclined with respect to the scan lines forming each scan plane Sn of the probe. Therefore, for each scan plane Sn, it will be performed the scanning for all scan lines that are coincident with or intersecting the corresponding line Ln of intersection between the single scan plane Sn of the probe and the section plane P along which the image is to be detected. This is shown in FIG. 13, where the two extreme scan lines SCNL(1) and SCNL(1+n) are illustrated.

FIG. 11 illustrates the less favourable condition, namely where the section plane P along which it is intended to detect the image completely cuts through the scanning planes Sn of the probe. In this condition, though it is necessary to scan all the lines of each scanning plane, the invention allows to focus the transmission signals on the intersection lines Ln between section plane P along which it is intended to detect the image and single scanning planes, obtaining considerable quality advantages. Also this situation is better illustrated in FIG. 14 where the scan lines SCNL(1) and SCNL(1+m) are shown.

Since, as will become clearer later, the processing for the extraction of features from the image along the required scanning plane, and the generation of the displayable image are performed with reference to the data relative only to the lines of intersection Ln between the plane P of section along which the image is to be detected and the scanning planes Sn of the probe, there are nevertheless considerable reductions in the total processing time with respect to the validation steps of the actual scanning plane along which the image is generated or the set of image data relative to said image suitable for the process of extraction of the desired features.

It is important to observe that this embodiment can be applied both to the decimated and/or undersampled and/or however reduced image data for the determination and validation of the scan plane, with reference to the anatomical markers that characterise the desired scan plane, and with respect to the generation of the set of image data that are relative to the validated scan plane and that constitute the image dataset to be used for the execution of the feature extraction processes.

Advantageously, it is possible to modify the focusing of the probe transmission signals along the different scan lines forming the Sn scan planes also in the case according to FIG. 10. In fact, knowing a priori the orientation and the length of the intersection lines Ln of the section plane P along which the image is to be detected with the scanning planes Sn of the probe, it is possible to vary the focusing law along the side-by-side section lines, so that for each scanning line of each scanning plane Sn, the transmitted beam is focused on the corresponding point of intersection with the corresponding line Ln.

Obviously, in order to ensure the detection of the desired image in any case, it is possible to perform the scanning for each scan plane Sn of the probe also along lines immediately adjacent to the scan lines that intersect the section plane P along which the image should be detected. This makes it possible to eliminate possible errors due to an imperfect correspondence between theoretical settings and the real situation and due, for example, to errors or tolerances in the definition of univocal references between the real position of the probe and the selected section plane along which the image has to be acquired. The above corresponds to the definition of a three-dimensional ROI that contains the image data of the desired scanning plane and, within the defined tolerances, also of other adjacent planes that are parallel or not to the desired scanning plane.

Figure 12:
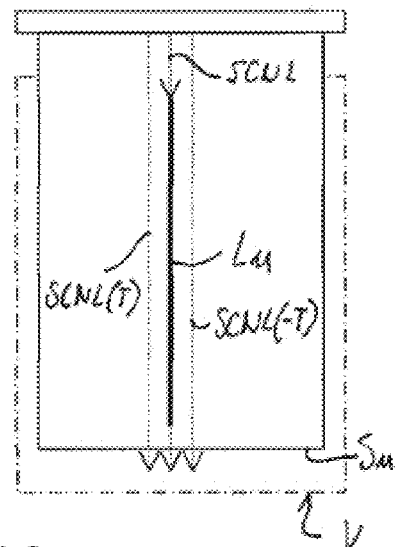
Figure 14:
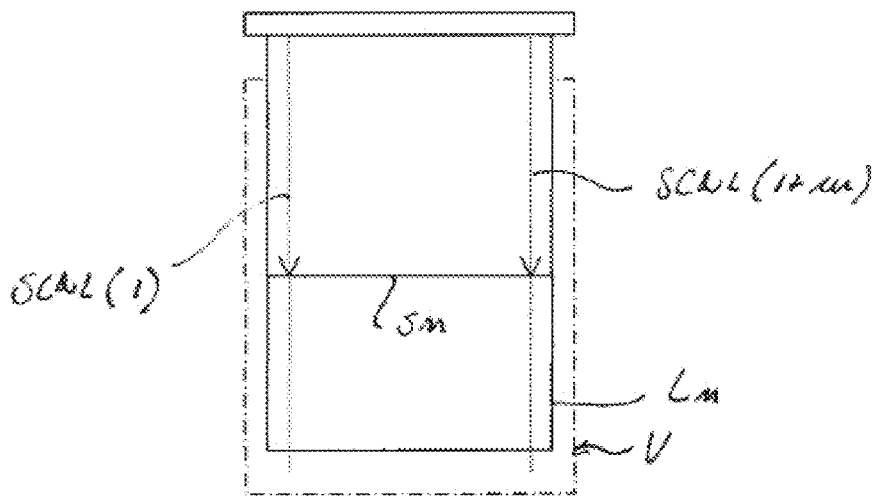

In any case, there is a reduction of the number of scanning lines performed for each scanning plane Sn of the probe. The above situation is illustrated in FIGS. 12 to 14 with the most extreme scanning lines and the delimitation lines of the area that have been scanned for security being indicated with SCNL(T) and SCNL(−T).

It should be noted that the method indicated above can also be applied to probes that have a two-dimensional transducer array and that therefore do not execute scans on planes, but rather along bands with a predetermined volume and that include at the same time several scanning planes side by side. In this case, the concept of a scan line can be applied to a unitary scan beam or volume.

According to a further improvement of the invention, whenever requested or compatible with the time required for the examination, it is possible to perform the entire scanning for each scanning plane Sn of the probe, by limiting the scanning parameters for the lines not intersecting or coinciding with the section plane P along which the image is to be detected, or possibly also the number of lines not intersecting said section plane P, in order to make faster both the scanning and the elaboration and saving at the expense of the quality, but obtaining anyway an image even of low quality of the zones not coinciding with the section plane P, that is outside a tridimensional ROI containing the said plane as defined above, along which it is required to detect the image. This image data can be combined with high quality image data along the section plane P. This can be helpful when the selected cross-sectional plane P along which the image is intended to be detected does not coincide in reality with the desired one and therefore it is possible to check whether slightly different settings of the orientation parameters of the cross-sectional plane P lead to the detection of the desired image.

According to an improvement of the above example, since the spatial correlation between the desired scan plane and the real scan planes depends on the relative positioning between the probe and the volume under examination, it is possible to perform an initial scout scan through which the position relationships are more precisely defined.

Figure 15:
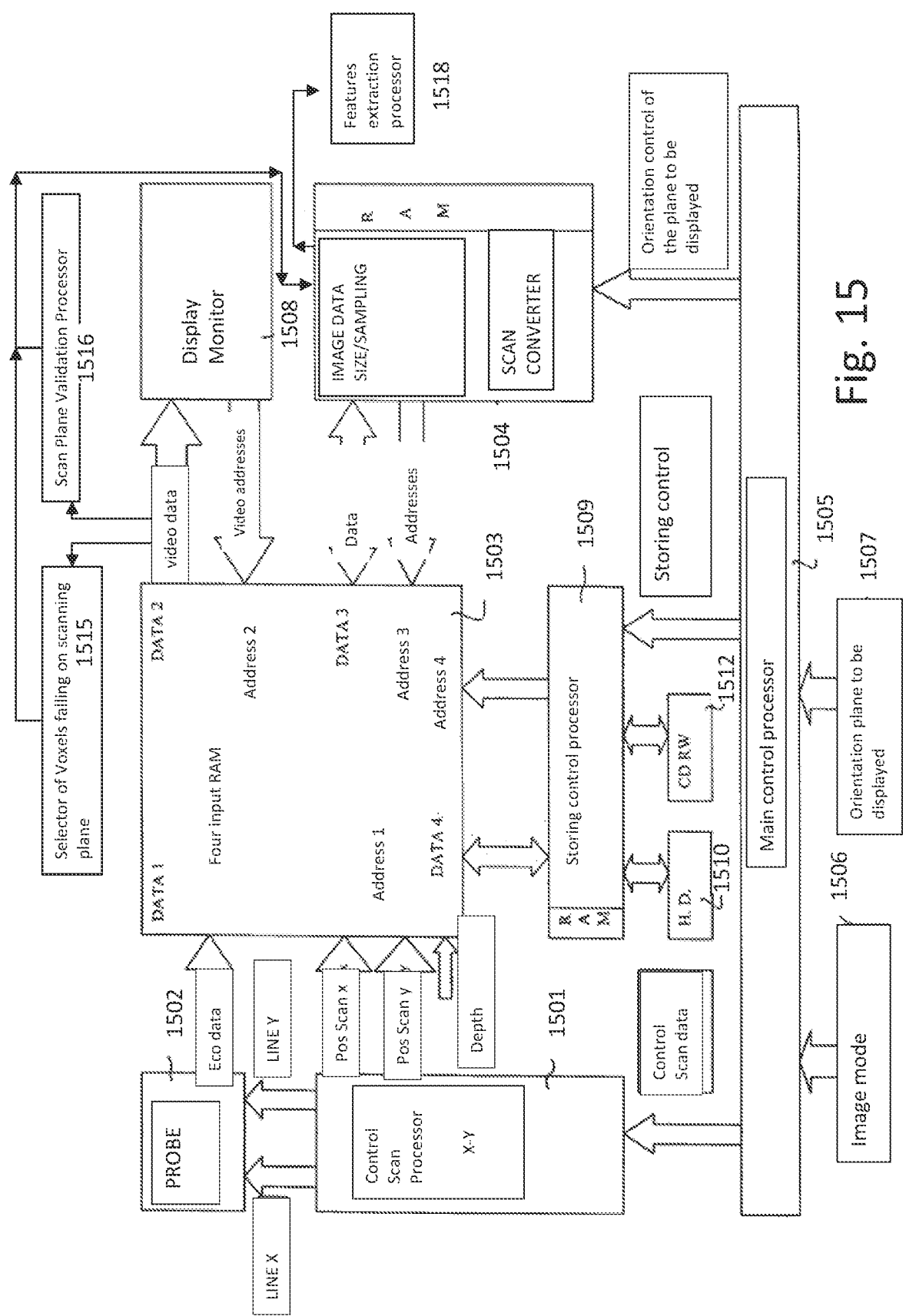
FIGS. 15 to 18 show a further detailed embodiment of an ultrasound imaging system that can be used for implementing the method according to the present invention.

FIG. 15 illustrates a very simplified block diagram of the construction of an ultrasound system that is configured to implement the embodiment of acquisition described above.

The system has a scanning control section comprising a scanning control processor 1501 to which is connected a probe 1502 for image acquisition, in particular a probe for three-dimensional acquisitions, for example but without limitation a probe of the phased-array-sector type.

In this case, the processor controls the position of the transducers in order to uniquely correlate the received echoes with the scanning plane and feeds the position data in space to a four-input RAM memory indicated with 1503. The position parameters (here referred to Cartesian coordinates but referable to any coordinate model for the definition of a volume), form the addresses 1 univocally correlated to the data input 1 of the RAM memory to which the probe supplies, after appropriate and usual processing, the data relative to the received echo signals. In this way, the memory 1503 becomes a three-dimensional matrix-like memory in which the memory spaces of the image data are defined by an address that corresponds or is correlated to the spatial location to which the image data refers.

With particular reference to the illustrated embodiment, but without limiting the applicability of the method and the device according to the invention, the acquisition occurs by lines according to two mutually orthogonal directions indicated with line x and line y while the third position coordinate is given by the depth. The Cartesian system is shown in FIGS. 9 to 11. Obviously, the fan-shaped scanning planes illustrated in FIGS. 9 to 11 are best described with reference to an angle. The transformation from one system to another is however constituted by a simple transformation between reference systems and is the application of a trivial transformation formula. The transformation from one system to another is however a simple transformation between reference systems and is the application of a trivial transformation formula. The third dimension related to depth is detectable or obtainable from the reflection time. The radio-frequency (RF) signal derived from the transduction of the echoes received for each scan line has a temporal development and the parts that arrive first are relative to lesser depths with respect to the signal parts that arrive at successive times for the same scan line.

Obviously, echo signals are appropriately sampled using a predefined time base in order to obtain discrete points. Discretization due to sampling, i.e. the sampling rate, affects the desired image definition.

The scan control processor is controlled by a main processor 1505 which is connected to means 1506 for setting the mode or type of image acquisition, such as B-mode, Doppler, Power Doppler or Harmonic Imaging, and to means 1507 for setting the orientation and/or position parameters of the section plane or projection plane to be displayed. Physically, these means may consist of knobs, selectors, keyboards, touch screen icons, etc. not illustrated in detail and possibly designed to load predefined orientation and position modes or parameters.

The main processor 1505 controls both the execution of the acquisition modes and therefore controls the scan control processor 1501 and a scan conversion processor, so-called scan-converter 1504 which, based on the orientation and/or position parameters of the predetermined scan plane suitable for extracting the features from the corresponding image determines the intersection lines L1, L2, L3, Ln of said scan plane P, i.e. the scan plane, suitable for extracting the desired features from the corresponding image, with individual scan planes, i.e., the position, orientation, and extent of an ROI containing said scan plane suitable for extracting desired features from the corresponding image, and identifies the memory addresses corresponding to the image data along said intersection lines, loads said data, and converts said data into control signals of a monitor 1508 by matching them to video addresses at the input/output addresses 3 and data 3 of the four-input RAM 1503. This data is read by the display monitor (data 2 and input 2 of the RAM 1503) and converted into image lines, thus forming the set of image lines relative to the predetermined scanning plane and suitable for extracting features from the corresponding image.

The data relating to the intersection lines L1, L2, L3, Ln of the predetermined scanning plane P and suitable for extracting features from the corresponding image, with the individual scanning planes Sn are also sent to the scanning control processor, for determining the scanning lines to be executed for each scanning plane Sn.

The scan-converter 1504 is of a type known and widely used in ultrasonic machines and is designed to process information with reference to a set of lines. It could therefore be a linear or two-dimensional scan-converter.

The implementation of the three-dimensional conversion, i.e., for scanning planes with any orientation in space, with reference to the volume under examination is achieved thanks to the combination of the linear or two-dimensional scan-converter with the main processor, with the scan control processor and with the four-input RAM memory, through which it is possible to save and recall the information collected during the scanning, keeping always an univocal correlation of the same with the correct position in space of said information, which is appropriately coded using the memory addresses of the data. During the processing, these are always uniquely identifiable with respect to the correct position in space and this guarantees the discrimination of the data inherent to the intersection lines of the predetermined scanning plane and suitable for the extraction of the features from the corresponding image with the scanning planes, for the read-out, the processing in display commands and the memorization in image data in said memory and finally for the recall of these image data for the steps of the method as described above with reference to FIG. 8.

A storage control processor 1509 is connected to the data inputs/outputs 4 of the RAM 1503 and controls always under command of the main processor 1505 the saving of data on physical storage media, such as Hard Disk 1510, Floppy, CD burners 1512.

As already described above, the method according to the invention is particularly effective with a type of so-called three-dimensional motorised scanning probes, although it must be noted that the implementation of the method is not limited to the use of such probes.

According to the present embodiment, a selector 1515 provides for the recall of the image data, in the form of a set of pixels or voxels from the output 2 of the RAM memory 1503 for the execution of the sequence of steps of the method according to FIG. 8 and in particular of the steps 603. The validation processor 1516 performs the step 604 and 605, while the unit 1504 comprises a section for varying the weight of the image data by selecting one or more ROIs and/or undersampling the image data and/or decimating the image data. The extraction of the features is assigned to a processing section indicated with 1518.

As already mentioned above, the sections or units for implementing the method according to one or more of the described embodiments and variant embodiments may be both of a purely software type, as it is contemplated that one of the processors 1501, 1505, 1509 and/or 1516 will execute at least part of a software containing instructions to make said processor suitable for performing the contemplated functions, and also of a hardware type, which provides for at least part of said software a dedicated and different processor present in the corresponding unit 1515 and/or 1516 and/or 1518. Even the program encoding the instructions for executing the machine learning algorithm can be executed by one or more of the processors included in the system, or it is possible to provide for a dedicated processor either integrated in the ultrasound system or provided in a remote station to which the ultrasound system can be connected by means of a communication unit, for example by cable or wireless and by means of known communication protocols.

Figure 16:
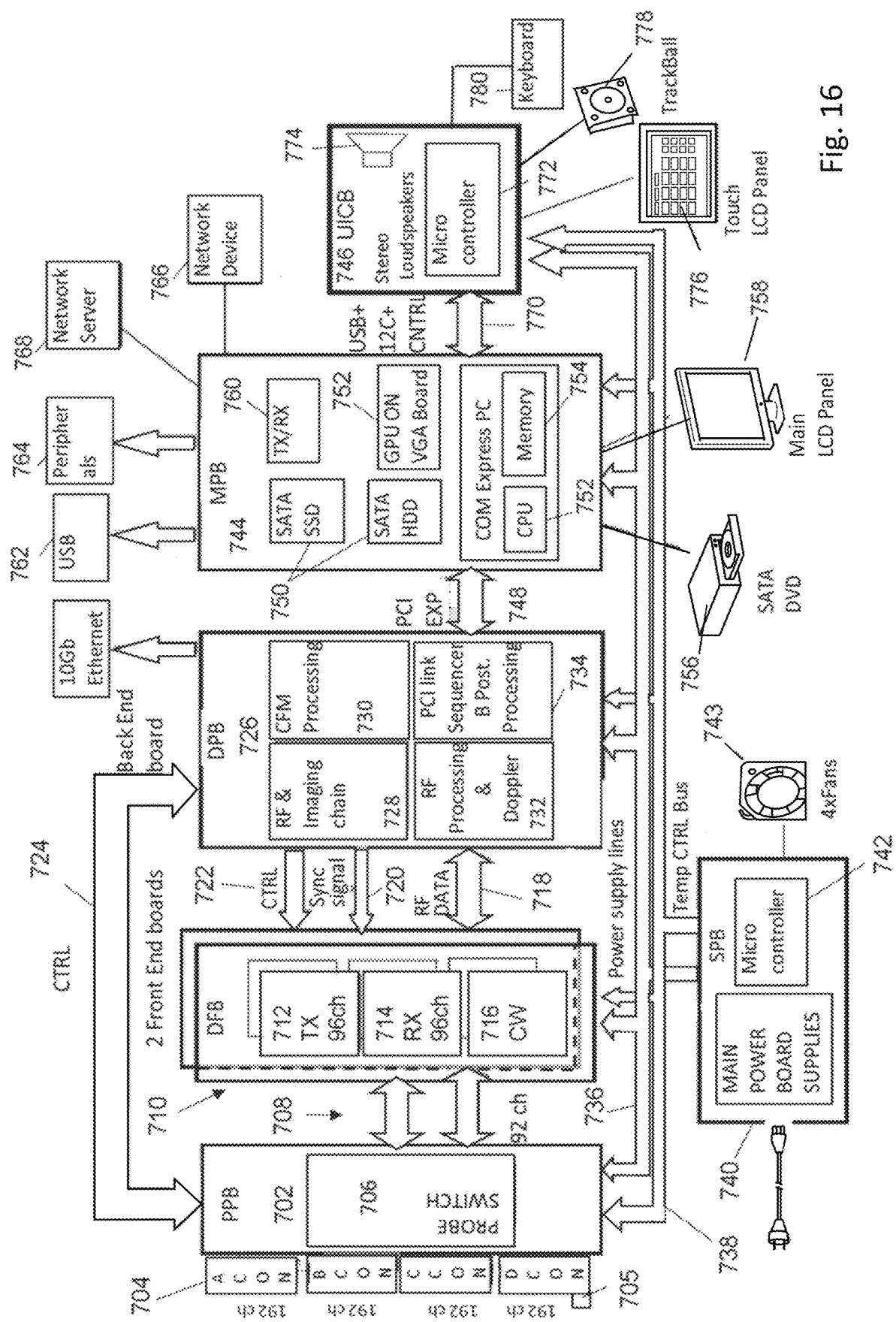
Figure 17:
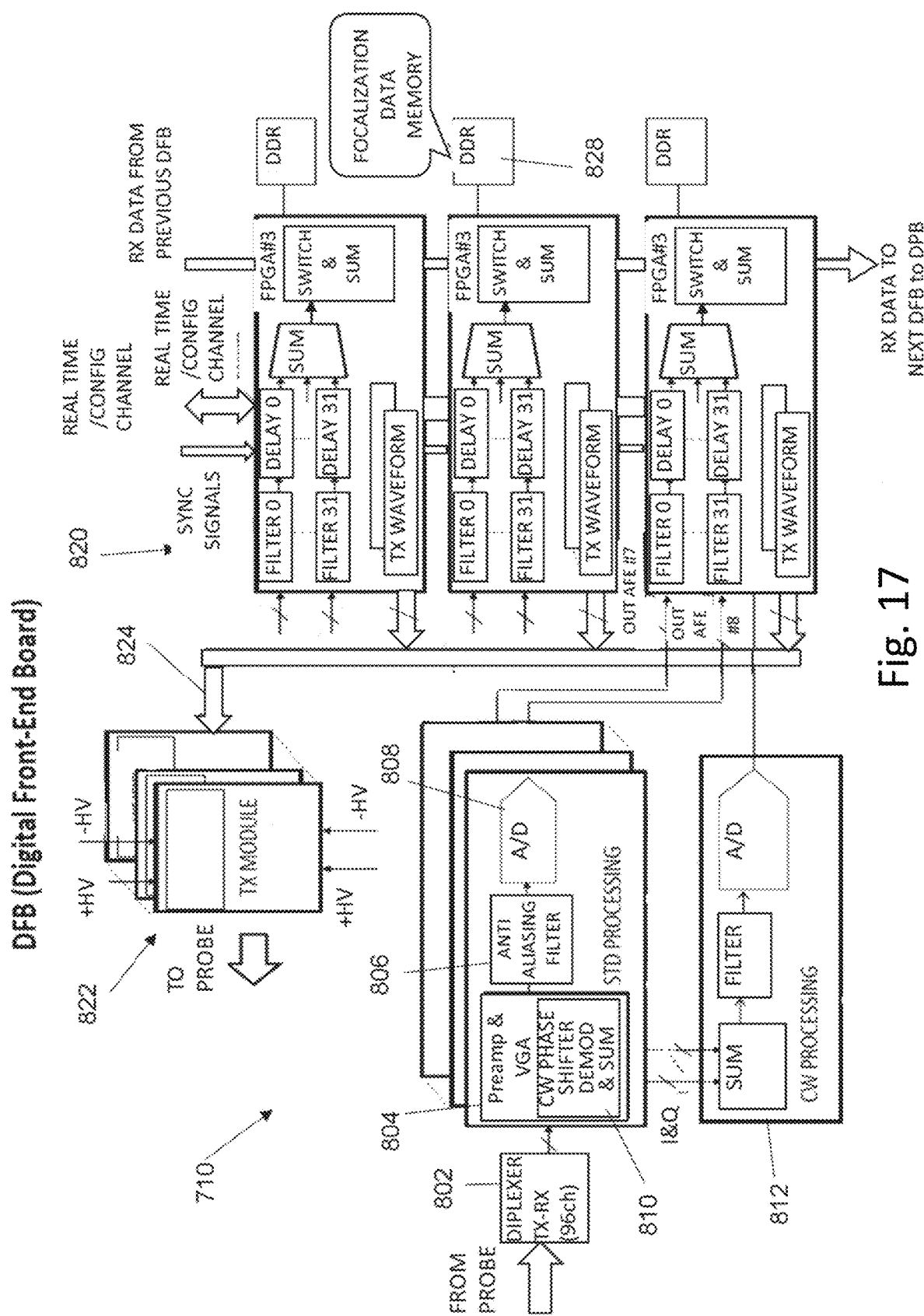
Figure 18:
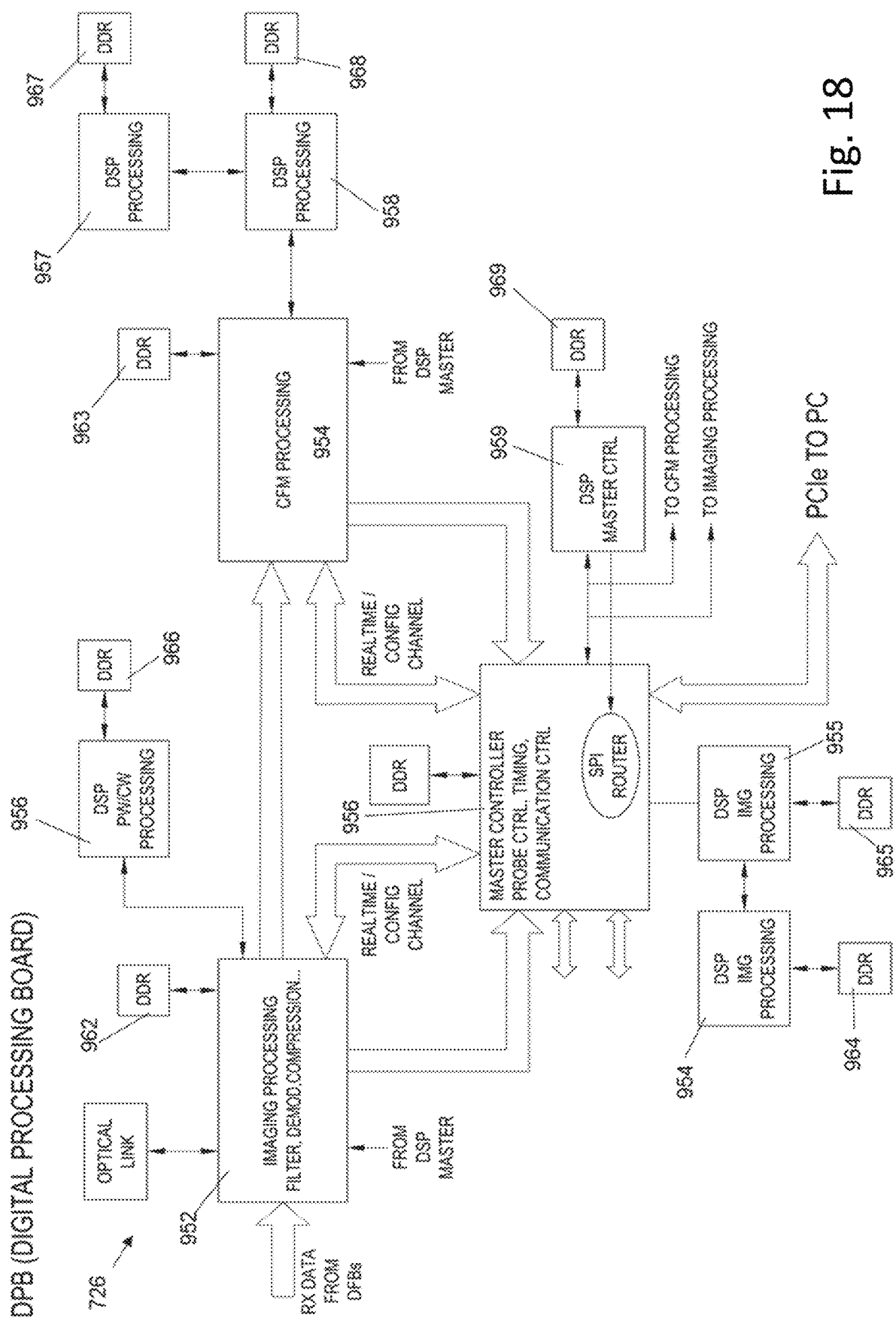

FIGS. 16 to 18 show an ultrasound system suitable for implementing the present invention according to one of the above variants.

FIG. 16 illustrates a block diagram of an ultrasonic system formed according to an alternative embodiment form. The system of FIG. 16 implements the operations described herein in relation to various forms of embodiment. By way of example, one or more circuits/processors within the system do implement the operations of possible processes illustrated in relation to the figures and/or described herein. The system includes a probe interconnection board 702 that includes one or more probe connection ports 704. The connection ports 704 can support various numbers of signal channels (e.g., 128, 192, 256, etc.). The connection ports 704 may be configured for use with different types of probe arrays (e.g., phased array, linear array, curved array, 1D, 1.25D, 1.5D, 1.75D, 2D array, etc.). The probes can be configured for different types of applications, such as abdominal, cardiac, maternity, gynecological, urological and cerebrovascular examination, breast examination, and the like.

The one or more connection ports 704 can support acquisition of 2D image data and/or the one or more connection ports 704 can support 3D image data. By way of example only, 3D image data can be acquired by physical movement (e.g., belt or doctor movement) of the probe and/or by a probe electrically or mechanically directing the transducer array.

The probe interconnection board (PIB) 702 includes a switching circuit 706 for selecting between connection ports 704. The switching circuit 706 can be manually operated depending on user inputs. For example, a user can designate a connection port 704 by selecting a button, switch, or another input of the system. Optionally, the user may select a connection port 704 by entering a selection through a user interface on the system.

Optionally, the switching circuit 706 can automatically switch to one of the connection ports 704 in response to the detection of the presence of a pairing connection of a probe. For example, the switching circuit 706 may receive a "connection" signal indicating that a probe has been connected to one of the selected connection ports 704. The connection signal may be generated by the probe when the probe is initially powered when coupled to the connection port 704.

Additionally or alternatively, each connection port 704 may include a sensor 705 that detects when a pairing connection on a probe cable has been interconnected with the corresponding connection port 704. The sensor 705 provides the connection signal to the switching circuit 706 and, in response thereto, the switching circuit 706 pairs the corresponding connection port 704 to the PIB outputs 708. Optionally, the sensor 705 can be constructed as a circuit with contacts provided to the connection ports 704. The circuit remains open when no contact connected to the corresponding connection port 704 is coupled. The circuit is closed when the counter-connector of a probe is connected to the connection port 704.

A control line 724 transmits control signals between the probe interconnection board 702 and a digital processing board 724. A power line 736 provides power from a power supply 740 to the various components of the system, including, but not limited to, the probe interconnection board (PIB) 702, the digital front-end boards (DFB) 710, the digital processing board (DPB) 726, the master processing board (M PB) 744, and a user interface control board (UI CB) 746. A temporary control bus 738 interconnects and provides temporary control signals between the power supply 740 and the boards 702, 710, 726, 744 and 746. The power supply 740 includes a cable to be coupled to an external AC power supply. Optionally, the power supply 740 may include one or more power storage devices (e.g., batteries) that provide power when AC power is interrupted or disconnected. The power supply 740 includes a controller 742 that controls the operation of the power supply 740, including the operation of the storage devices.

Additionally or alternatively, the power supply 740 can include alternative power sources, such as solar panels and the like. One or more fans 743 are coupled to the power supply 740 and are controlled by the controller 742 for being turned on and off according to the operating parameters (e.g., temperature) of the various printed circuit boards and electronic components within the whole system (e.g., to prevent overheating of the various electronic components).

The digital front-end boards 710 provide the analog interface to and from the probes connected to the probe interconnection board 702. The DFB 710 also provides pulse or control and drive signals, controls analog gains, includes analog to digital converters in connection with each receive channel, provides the management of transmit beamforming and the management of receive beamforming and the composition of the vector (associated with focusing during receive operations).

The digital front boards 710 include transmission driver circuits 712 that generate transmission signals that are passed on corresponding channels to corresponding transducers in connection with ultrasonic transmission capture operations. The transmission driver circuits 712 provide pulses or control for each drive signal and transmit the beamforming management to guide firing operations to points of interest within the region of interest. For instance, a transmission circuit 712 can be provided separately in connection with each individual channel, or a common transmission circuit 712 can be used to drive multiple channels. The transmission circuits 712 cooperate in order to focus the transmission beams on one or more selected points within the region of interest. The transmission circuits 712 can implement the single line transmission, coded firing sequences, multi-line transmission operations, ultrasonic beam generation that can induce shear waves, and other forms of ultrasonic transmission techniques.

The digital front end boards 710 include beamformer receiver circuits 714 that receive the echo/reception signals and perform various analog and digital processing on them, as well as phase shifting, time delay and other operations in connection with beamforming. The beamformer circuits 714 can implement various types of beamforming, such as single-line acquisition, multi-line acquisition, and other ultrasonic beamforming techniques.

Digital front end cards 716 include continuous wave Doppler processing circuits 716 configured to perform continuous wave Doppler processing on received echo signals. Optionally, the continuous wave Doppler circuits 716 may also generate continuous wave Doppler transmission signals.

The digital front-end boards 710 are coupled to the digital processing board 726 through several Buses and control lines, such as the control lines 722, the synchronization lines 720, and one or more data Buses 718.

Control lines 722 and synchronization lines 720 provide control and data information, as well as synchronization signals, to transmit drive circuits 712, to receive beamforming circuits 714 and to continuous wave Doppler circuits 716. The data bus 718 transmits RF ultrasound data from the digital front-end boards 710 to the digital processing board 726. Optionally, digital front-end cards 710 can convert RF ultrasonic data into I,Q data pairs that are then passed to digital processing card 726.

The digital processing board 726 includes an RF and imaging processing module 728, a colour flow processing module 730, an RF and Doppler processing module 732, and a PCI connection module 734. The digital processing board 726 performs RF filtering and processing, processing of black and white image information, processing in connection with colour flow, processing in Doppler mode (e.g. in connection with Doppler probing and continuous wave Doppler). The digital processing board 726 also provides image filtering (e.g. speckle reduction) and scanner timing control. The digital processing board 726 may include other modules based on the ultrasound image processing functionality provided by the system.

Modules 728-734 include one or more processors, DSP and/or FPGAs and the instructions of the memory storage program to address the processors, DSPs and/or FPGAs to perform various ultrasound image processing operations. The RF and imaging module 728 performs various ultrasound-related imaging operations, such as B-mode image processing of the RF data. The RF processing and Doppler module 732 converts the incoming RF data into I, Q data pairs, and performs Doppler-related processing on the I, Q data pairs. Optionally, the imaging module 728 can perform B-mode image processing on I, Q data pairs. The CFM processing module 730 performs colour flow image processing on the ultrasonic RF data and/or the I, Q data pairs. The PCI link 734 manages the transfer of ultrasonic data, control data, and other information, on a PCI express bus 748, between the digital processing card 726 and the master processing card 744.

The master processing card 744 includes memory 750 (e.g., serial ATA solid state devices, serial ATA hard drives, etc.), a VGA card 752 that includes one or more graphics processing units (GPUs), one or more transceivers 760 one or more CPUs 752 and the memory 754. The master processing board (also known as the PC board) provides the control of the user interface, the scan conversion and the cine loop management. The master processing board 744 can be connected to one or more external devices, such as a DVD player 756, and one or more displays 758. The master processing board includes communication interfaces, such as one or more USB ports 762 and one or more ports 764 configured to be coupled to peripheral devices. The master processing board 744 is configured to maintain communication with various types of network devices 766 and various network servers 768, such as by wireless connections through the transceiver 760 and/or through a network connection (e.g., through the USB connector 762 and/or the peripheral connector 764).

The network devices 766 can represent portable or desktop devices, such as smartphones, personal digital assistants, tablet devices, laptop computers, desktop computers, smart watches, ECG monitors, patient monitors, and the like. The master processing board 744 transmits ultrasound images, ultrasound data, patient data and other information and content to the network devices for presentation to the user. The master processing card 744 receives, from the network devices 766, input, requests, data entry and the like.

The network server 768 may represent part of a medical network, such as a hospital, a healthcare network, a third party healthcare provider, a medical equipment maintenance service, a medical equipment manufacturer, a government healthcare service, and the like. The communication link with the network server 768 may be established via the Internet, a private intranet, a local area network, a wide area network, and the like.

The master processing board 744 is connected to the master processing board 744 via a communication link 770 with a user interface control board 746. The communication link 770 transmits data and information between the user interface and the master processing board 744. The user interface control board 746 includes one or more processors 772, one or more audio/video components 774 (e.g., speakers, a display, etc.). The user interface control board 746 is coupled to one or more user interface input/output devices, such as an LCD touch screen 776, a trackball 778, a keyboard 780, and the like. The processor 772 manages the operation of the LCD touch screen 776, in addition to collecting user inputs through the touch screen 776, the trackball 778, and the keyboard 780, wherein such user inputs are routed to the master processing board 744 in connection with the implementation of these embodiments.

FIG. 17 illustrates a block diagram of a part of the digital boards 710 formed according to the embodiments contained herein. A diplexer assembly 802 receives the ultrasonic signals for individual channels via the PIB output 808. The ultrasonic signals are transmitted along a standard processing circuit 805 or to a continuous wave processing circuit 812, depending on the type of probe used. When processed by the standard processing circuit 805, a preamplifier and a variable gain amplifier 804 process the incoming ultrasound and receive the ultrasonic signals which are then fed to an anti-aliasing filter 806 which performs anti-aliasing filtering. Its output is fed to an A/D converter 808 which digitises the incoming analogue ultrasound reception signals. When a continuous wave (CW) probe is used, the resulting signals are fed to a demodulator for demodulation and summing 810 which converts the analog RF receive signals into CW data pairs I,Q.

The CW data pairs I,Q are summed, filtered and digitized by a continuous wave processing circuit 812. The outputs from the standard or continuous wave processing circuits 805, 812 are then fed to the beamforming circuits 820 which use one or more FPGAs to filter, delay and sum the incoming digitized reception signals before feeding the RF data to the digital processing board 826 (FIG. 16). The FPGAs receive the focusing data from the memories 828. The focus data are used to manage the filters, delays and summing operations performed by the FPGAs in relation to beamforming. The RF data under formation are fed between the beamforming circuits 820 and finally to the digital processing board 726.

The digital front-end boards 710 also include transmission modules 822 that provide transmission signals to the corresponding transducers of the ultrasound probe. The beamforming circuits 820 include the memory that stores the transmission waveforms. The transmission modules 822 receive the transmission waveforms on the line 824 from the beamforming circuits 820.

FIG. 18 illustrates a block diagram of the digital processing board 726 implemented according to the embodiments of the present disclosure. The digital processing board 726 includes several processors 952-959 for performing various operations under the control of program instructions saved in corresponding memories, see 962-969. A master controller 950 manages the operation of the digital processing board 726 and the processors 952-959. For example, one or more processors such as 952 can perform the filtering, compounding, modulation, compression and other operations, while another processor 953 performs the colour flow processing. The master controller provides control signals for the probe, timing control signals, communications control signals, and the like. The master controller 950 provides real-time configuration information and synchronization signals in connection with each channel to the digital front-end board 710.

It should be clearly understood that the various arrangements and processes widely described and illustrated with reference to the figures, and/or one or more individual components or elements of such arrangements and/or one or more process operations associated with such processes, can be applied independently of or in conjunction with one or more other components, elements and/or process operations described and illustrated herein. Accordingly, while the various arrangements and processes are widely contemplated, described and illustrated herein, it should be understood that they are provided in a merely illustrative and non-restrictive manner, and can further be considered as mere examples of possible work environments in which one or more of the arrangements or processes can operate or function.

These aspects are described herein by reference to Figures, which illustrate example methods, devices and program products according to various embodiments. These program instructions may be provided to a processor of a standard computer, of a special purpose computer or of another programmable data processing or information managing device in order to create a machine, so that the instructions executed by a processor of the device can implement the specified functions/acts. The program instructions may also be stored in a device readable medium that can direct a device to operate in a specified manner, such that the instructions stored in the device readable medium produce an item of manufacture, including instructions that implement the specified function/action. The program instructions may also be loaded onto a device to cause a series of operational steps to be executed on the device to produce a process implemented on the device such that the instructions executing on the device provide processes for implementing the specified functions/actions.

One or more of the operations described above in relation to methods can be performed using one or more processors. The various devices in the systems described herein may represent one or more processors, and two or more of these devices may include at least one of the same processors. In one embodiment, the operations described herein may represent actions performed when one or more processors (e.g., of the devices described herein) execute program instructions stored in memory (e.g., software stored on a tangible, non-transitory computer-readable storage medium, such as a computer hard drive, ROM, RAM, or the like).

The computer or computers may execute a series of instructions which are stored in one or more storage elements in order to process data. The storage elements may also store data or other information as required. The storage element may be in the form of an information source or a physical memory element within the controllers and the control device. The set of instructions may include various commands that instruct the controllers and the control device to perform specific operations such as the methods and processes of the various embodiments of the subject matter described herein. The set of instructions may be in the form of a software program. The software may be in various forms, such as system software or application software. In addition, software may be in the form of a set of separate programs or modules, a program module within a larger program or a part of a program module. The software may also include a modular programming in form of object-oriented programming. The processing of input data by the processing machine may be in response to user commands, or in response to the results of previous processing, or in response to a request made by another processing machine.

The controller may include any processor or microprocessor based system, including systems using microcontrollers, reduced instruction set computers (RISC), application specific integrated circuits (ASICs), field programmable gate arrays (FPGAs), logic circuits and any other circuit or processor able to perform the functions described herein. When the controller is processor-based, it executes the program instructions stored in memory to perform the corresponding operations. In addition or in alternative, controllers and the control device may represent circuits that can be implemented as hardware. The above examples are exemplary only and are not intended to limit in any way the definition and/or meaning of the term 'controller'.

Optionally, aspects of the processes described herein may be performed on one or more network servers. The network may support communications using any of a variety of commercially available protocols, such as Transmission Control Protocol/Internet Protocol ("TCP/IP"), User Datagram Protocol ("UDP"), protocols operating at various levels of the Open System Interconnection ("OSI") model, File Transfer Protocol ("FTP"), Universal Plug and Play ("UpnP"), Network File System ("NFS"), Common Internet File System ("CIFS") and AppleTalk. The network may be, for example, a local area network, a wide area network, a virtual private network, internet, an intranet, an extranet, a public switched telephone network, an infrared network, a wireless network, a satellite network, and any combination thereof.

In implementations using a web server, the web server may execute any of a variety of server or mid-level applications, including Hypertext Transfer Protocol ("HTTP") servers, FTP servers, Common Gateway Interface ("CGI") servers, data servers, Java servers, Apache servers and enterprise application servers. The servers may also be able to execute programs or scripts in response to requests from user devices, for example by running one or more web applications that may be implemented as one or more scripts or programs written in any programming language, such as Java®, C, C# or C++, or any scripting language, such as Ruby, PHP, Perl, Python or TCL, as well as combinations thereof. Servers may also include database servers, including, without limitation, those commercially available from Oracle®, Microsoft®, Sybase® and IBM®, as well as open-source servers such as MySQL, Postgres, SQLite, MongoDB, and any other server capable of storing, retrieving and accessing structured or unstructured data. Database servers may include table-based servers, document-based servers, unstructured servers, relational servers, non-relational servers or combinations thereof, and/or other database servers.

The embodiments described herein may include a variety of data archives and other memory and storage media as discussed above. These may be located in a variety of places, such as on a storage medium local to (and/or resident on) one or more computers or remote from one or all computers on the network. In a particular set of embodiments, information may reside in a network of storage areas ("SAN") familiar to those skilled in the art. Similarly, any files needed to perform the functions assigned to computers, servers or other network devices may be stored locally and/or remotely, as appropriate. In the case where a system comprises computer devices, each such device may include hardware elements which may be electrically coupled via a bus, the elements comprising, for example, at least one central processing unit ("CPU" or "processor"), at least one input device (e.g., a mouse, keyboard, controller, touch screen or keyboard) and at least one output device (e.g., a display device, printer or speaker). Such a system may also include one or more storage devices, such as disk drives, optical storage devices, and solid-state storage devices such as random access memory ("RAM") or read-only memory ("ROM"), as well as removable media devices, memory cards, flash cards, etc.

Such devices may also include a reader for computer-readable storage media, a communication device (e.g., a modem, a network card (wireless or wired)), an infrared communication device, etc. The reader of computer-readable storage media may be connected or configured to receive a computer-readable storage media, representing remote, local, fixed and/or removable storage devices, as well as storage media for temporarily and/or more permanently containing, storing, transmitting and retrieving computer-readable information. The system and the various devices will also include a number of software applications, modules, services or other elements located within at least one working memory device, including an operating system and application programs, such as a client application or web browser. It should be appreciated that alternative embodiments may have numerous variations on those described above. For example, custom hardware may also be used and/or particular elements may be implemented in hardware, software (including portable software, such as applets) or both. In addition, connection to other computer devices as network input/output devices may be used.

The various embodiments may further comprise receiving, sending or storing instructions and/or data implemented according to the above description on a computer readable medium. Storage media and computer-readable media for containing code, or portions of code, may include any appropriate media known or used in the art, including, but not limited to, volatile and non-volatile, removable and non-removable media implemented in any method or technology for storing and/or transmitting information such as computer-readable instructions, data structures, program modules or other data, including RAM, ROM, Electrically Erasable Programmable Read-Only Memory ("EEPROM"), Flash Memory or other memory technology, Compact Disc Read-Only Memory ("CD-ROM"), Digital Versatile Disc (DVD) or other optical storage devices, magnetic cassettes, magnetic tape, magnetic disk storage or other magnetic storage devices or any other medium that can be used to store desired information and can be accessed by the system device. Based on the disclosure and teachings provided herein, a person of ordinary skill in the art will appreciate other ways and/or methods of realizing the various embodiments.

The specifications and drawings are, accordingly, to be considered in an illustrative rather than restrictive sense. It will, however, be apparent that various modifications and changes may be made herein without departing from the broader spirit and scope of the invention as set forth in the claims.

Other variations are within the spirit of the present disclosure. Thus, while the disclosed techniques are susceptible to various modifications and alternative constructions, some of their illustrated embodiments are shown in the drawings and have been described in detail above. It should be understood, however, that there is no intention to limit the invention to the specific form or forms disclosed, but on the contrary, the intention is to cover all modifications, alternative constructions and equivalents that fall within the spirit and scope of the invention as defined in the appended claims.

The use of the terms "a" and "an" and "the" and similar referents in the context of the description of the disclosed embodiments (especially in the context of the following statements) should be interpreted to cover both singular and plural, unless otherwise indicated herein or clearly contradicted by the context. The terms "comprising", "having", "including" and "containing" are to be interpreted as unlimited terms (i.e., meaning "including, but not limited to"), unless otherwise indicated. The term "connected", when unmodified and referring to physical connections, shall be understood as being partially or wholly contained within, connected or joined, even if there is something intervening. The citation of ranges of values herein is intended merely as a condensed method for individually referring to each separate value that falls within the range, unless otherwise stated herein, and each separate value is incorporated into the specification as if it were individually cited herein. The use of the term "set" (e.g. "a set of elements") or "subset", unless otherwise indicated or contradicted by the context, shall be understood as a non-empty collection comprising one or more members. Furthermore, unless otherwise indicated or contradicted by the context, the term "subset" of a corresponding set does not necessarily indicate a suitable subset of the corresponding set, but the subset and the corresponding set may be equal.

The operations of the processes described herein may be performed in any appropriate order, unless otherwise stated herein or clearly contradicted by the context—The processes described herein (or variations and/or combinations thereof) may be executed under the control of one or more computer systems configured with executable instructions and may be implemented as code (e.g., executable instructions, one or more computer programs, or one or more applications) that are executed collectively on one or more processors, by hardware, or combinations thereof. The code may be stored on a computer readable storage medium, for example in the form of a computer program comprising a plurality of instructions executable by one or more processors. The computer readable storage medium may be non-transitory.

Preferred embodiments of this disclosure are described in the present document, including the best mode known to the inventors to implement the invention. Variations of such preferred embodiments may become apparent to those of ordinary skill in the art by reading the foregoing description. The inventors expect that skilled artisans will use such variations in an appropriate manner, and the inventors intend that the embodiments of the present disclosure to be practiced in a manner different from that specifically described herein. Accordingly, the scope of the present disclosure includes all modifications and equivalents of the object recited in the appended claims as permitted by applicable law. Further, any combination of the foregoing elements in all possible variations is included within the scope of the present disclosure unless otherwise indicated herein or clearly contradicted by the context.

All references, including publications, patent applications and patents, cited herein are incorporated herein by reference to the same extent that each reference has been individually and specifically indicated to be incorporated by reference and disclosed in its entirety in the present document.

Although it is disclosed primarily with reference to images composed of ultrasound, the technique of motion compensation disclosed herein may also be used in other types of image processing, particularly where moving images must be combined in some way, such as in differential contrast imaging techniques, in persistence processing, or the like. Ultrasound is not the only imaging modality that may benefit from the present teachings. X-ray, MRI, SPECT, CT images can also be used as well as video images in non-medical fields such as video compression, the segmentation of video objects, the analysis of video content and the frame interpolation or in applications where 'movement' between images may only be apparent such as in image registration or 3D stereo matching.

The invention claimed is:

1. Method for determining scan planes in the acquisition of ultrasound images, comprising:
    a) defining a body to be examined and defining a predetermined orientation and/or a predetermined position of a predetermined section plane which intersects said body at a desired location;
    b) performing a three-dimensional volumetric ultrasound scan of said body by acquiring a plurality of scan planes via an ultrasound probe to acquire a volumetric ultrasound image comprising three-dimensional image data;
    c) providing a machine learning algorithm for the identification of the image data from the volumetric ultrasound image that fall along said predetermined section plane that has the predetermined orientation and/or the predetermined position with respect to said body under examination and which said predetermined section plane intersects the volumetric ultrasound image, said machine learning algorithm being trained with a database of known cases to identify which data contributions of the image data from the volumetric ultrasound image fall on said predetermined section plane, or which of voxels that make up the image data of the volumetric ultrasound image fall on said predetermined section plane;
    d) for each scan plane of the plurality of acquired scan planes, identifying the data contributions to the image data or the voxels that fall along the said predetermined section plane by means of the said machine learning algorithm according to step c) and generating therefrom a set of image data along the said predetermined section plane, said set of image data corresponding to a respective line of intersection between said predetermined section plane and each scan plane of the plurality of acquired scan planes;

e) storing said set of image data identified as falling along said predetermined section plane or subjecting said set of image data to further processing; and f) determining, via the machine algorithm, the correspondence between a position and/or an orientation of a scan plane of the plurality of acquired scan planes with the predetermined position and/or predetermined orientation of the said predetermined section plane, and/or a correspondence between said set of image data related to the data contributions or the voxels that derive from or fall on the respective line of intersection between each scan plane of the plurality of acquired scan planes and the predetermined section plane.

2. Method according to claim 1, further comprising the steps of:

g) calculating a reliability of said set of image data with reference to the predetermined section plane and report this value to a user;

h) repeating the acquisition of the volumetric ultrasound image by step b) and/or the identifying step d) of the image data contributions or the voxels that fall on the said predetermined section plane and perform step g) in relation to the newly identified image data contributions;

i) carrying out step h) until a fitness value falls within a predetermined range of values;

j) proceeding with step e) if the fitness value falls within said predetermined range of values.

3. Method according to claim 1, wherein verification of the position and/or the orientation of said scan plane or said set of image data which falls on the predetermined section plane which intersects said volumetric ultrasound image are performed on the three-dimensional image data comprising individual pixels or voxels.

4. Method according to claim 3, wherein the number of pixels or voxels along said scan plane is reduced by resolution reduction and/or image compression techniques.

5. Method according to claim 3, in which, following verification of the position and/or the orientation of said scan plane and/or said set of image data using the pixels or voxels of the volumetric ultrasound image, the steps of image data processing and/or of features extraction are performed by returning to a higher resolution and/or decompressing the volumetric ultrasound image along the predetermined section plane at an original resolution, said set of image data being in the form of raw data from the image data acquired in step b), or derived from corresponding RF signals.

6. Method according to claim 1, wherein prior to verification of the position and/or orientation of said scan plane or said set of image data comprising pixels or voxels of the volumetric ultrasound image which fall on the predetermined section plane, the method further comprises selecting a subset of scan planes from the at least one scan place and/or a subset of image data from the image data of the volumetric ultrasound image that fall into a limited region and/or a limited region of the body under examination, a ROI, which contains target regions and/or target structures and/or target tissues.

7. Method according to claim 6, wherein, a position and/or an orientation of said ROI is determined on the basis of recognition of one or more anatomical markers that are characteristic markers that correspond to anatomical structures present in the body under examination and close to or coinciding with the predetermined section plane.

8. Method according to claim 7, wherein the recognition of the said anatomical structures or of the said characteristic markers, is performed on the basis of a processing of the image data from the volumetric ultrasound image in any of forms chosen from raw data and corresponding radio frequency signals, modified or compressed to a resolution lower than that of acquisition in step b).

9. Method according to claim 8, wherein image processing algorithms are used for the recognition of said anatomical structures and are chosen from autocorrelation algorithms, classification algorithms of both statistical and deterministic type and also machine learning algorithms.

10. Method according to claim 6, wherein an acquisition at resolution lower than a subsequent resolution is provided which is subjected to a processing for determination of size, position and orientation of a ROI in the form of a bounding box, a subsequent acquisition with higher resolution of the image of the region included within the bounding box.

11. Method according to claim 1, wherein said method is applied to the obstetric field and the acquisition of the volumetric ultrasound image in step b) comprises acquiring ultrasound images for carrying out measurements of characteristic quantities of organs of the fetus and hence for an estimation of the fetal weight or other characteristics of the fetus.

* * * * *